(12) United States Patent
Pagano et al.

(10) Patent No.: US 9,796,681 B2
(45) Date of Patent: Oct. 24, 2017

(54) TETRAHYDROISOQUINOLINES AS SELECTIVE NADPH OXIDASE 2 INHIBITORS

(71) Applicant: University of Pittsburgh—Of the Commonwealth System of Higher Education, Pittsburgh, PA (US)

(72) Inventors: Patrick J. Pagano, Sewickley, PA (US); Peter Wipf, Pittsburgh, PA (US); Maria E. Cifuentes-Pagano, Sewickley, PA (US); Erin M. Skoda, Columbia, MD (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 14/888,390

(22) PCT Filed: May 1, 2014

(86) PCT No.: PCT/US2014/036402
§ 371 (c)(1),
(2) Date: Oct. 30, 2015

(87) PCT Pub. No.: WO2014/179592
PCT Pub. Date: Nov. 6, 2014

(65) Prior Publication Data
US 2016/0083351 A1 Mar. 24, 2016

Related U.S. Application Data

(60) Provisional application No. 61/818,726, filed on May 2, 2013.

(51) Int. Cl.
| | |
|---|---|
| C07D 221/22 | (2006.01) |
| A61K 31/4748 | (2006.01) |
| C07D 453/06 | (2006.01) |
| A61K 45/06 | (2006.01) |
| C07D 401/06 | (2006.01) |
| C07D 405/10 | (2006.01) |
| C07D 409/06 | (2006.01) |
| C07D 413/06 | (2006.01) |

(52) U.S. Cl.
CPC ........ *C07D 221/22* (2013.01); *A61K 31/4748* (2013.01); *A61K 45/06* (2013.01); *C07D 401/06* (2013.01); *C07D 405/10* (2013.01); *C07D 409/06* (2013.01); *C07D 413/06* (2013.01); *C07D 453/06* (2013.01)

(58) Field of Classification Search
CPC .......... C07D 221/22; A61K 31/4748
USPC ....................................... 546/79
See application file for complete search history.

(56) References Cited

PUBLICATIONS

Yu. N. Bubnov et al 2001, Russian Chemical Bulletin, Allymetallation of benzoazheterocycles with allylic derivatives of Zinc.*
Bubnov et al., "Allylic Boron and Zinc Derivatives in Synthesis and Transformations of Nitrogen Heterocycles," *Pure and Applied Chemistry*, 2000, vol. 72, pp. 1641-1644.
Bubnov et al., "Allylmetallation of Benzoazaheterocycles with Allylic Derivatives of Zinc. Synthesis of 1,4-ethano-2,3-dihidroisoquinolines and Allylated Heterocycles," *Russian Chemical Bulletin*, Nov. 2001, vol. 50, Issue 11, pp. 2172-2182.
Cifuentes-Pagano et al., "Bridged Tetrahydroisoquinolines as Selective NADPH Oxidase 2 (Nox2) Inhibitors," *Medchemcomm.*, Jul. 2013, vol. 4, No. 7, pp. 1085-1092, author manuscript 19 pp.
Cifuentes-Pagano et al., "Sly as a Nox: The Challenges, Triumphs, and Pitfalls of Selective NADPH Oxidase," *Antioxidants & Redox Signaling*, 2013, doi: 10.1089/ars.2013/5620, proof, 40 pp.
Cifuentes-Pagano et al., "The Quest for Selective Nox Inhibitors and Therapeutics: Challenges, Triumphs and Pitfalls," *Antioxidants & Redox Signaling*, Jun. 10, 2014, vol. 20, No. 17, pp. 2741-2754.

(Continued)

*Primary Examiner* — Rita Desai
(74) *Attorney, Agent, or Firm* — Klarquist Sparkman, LLP

(57) ABSTRACT

Embodiments of bridged tetrahydroisoquinolines and methods for their use in selectively inhibiting nicotinamide adenine dinucleotide phosphate (NADPH) oxidase 2 are disclosed. The disclosed compounds have a structure according to general formula I or a pharmaceutically acceptable salt thereof:

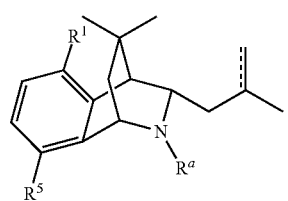

(I)

wherein "------" represents a single or double bond, $R^1$ is hydrogen, halogen, lower aliphatic, substituted or unsubstituted aryl, or substituted or unsubstituted heteroaryl; $R^a$ is hydrogen, —$CH_2R^2$, $R^3$, or —$SO_2R^4$; $R^2$ is lower aliphatic, substituted or unsubstituted aryl, or substituted or unsubstituted heteroaryl; $R^3$ is substituted or unsubstituted aryl, or substituted or unsubstituted heteroaryl; $R^4$ is lower aliphatic, or substituted or unsubstituted aryl; and $R^5$ is hydrogen, halogen, or lower aliphatic.

12 Claims, 8 Drawing Sheets

(56) References Cited

PUBLICATIONS

International Search Report and Written Opinion, dated Aug. 14, 2014, issued in corresponding International Application No. PCT/US2014/036402.
STN Chemical Abstracts Registry No. 774176-66-8, STN entry date Nov. 3, 2004, 1,2,3,4-tetrahydro-2,2,9,9-tetramethyl-3-(2-methyl-2-propen-1-yl)-1,4-Ethanoisoquinolinium.

* cited by examiner

TETRAHYDROISOQUINOLINES AS SELECTIVE NADPH OXIDASE 2 INHIBITORS

CROSS REFERENCE TO RELATED APPLICATIONS

This is the U.S. National Stage of International Application No. PCT/US2014/036402, filed May 1, 2014, which was published in English under PCT Article 21(2), which in turn claims the benefit of U.S. Provisional Application No. 61/818,726, filed May 2, 2013, each of which is incorporated by reference in its entirety herein.

ACKNOWLEDGMENT OF GOVERNMENT SUPPORT

This invention was made with government support under HL079207, HL003455 and GM067082 awarded by the National Institutes of Health. The government has certain rights in the invention.

FIELD

The present disclosure concerns bridged tetrahydroisoquinolines and methods for their use in selectively inhibiting nicotinamide adenine dinucleotide phosphate (NADPH) oxidase 2.

BACKGROUND

Oxidative stress remains a central causative factor in the etiology and progression of myriad vascular and non-vascular diseases, including among many others cardiovascular diseases, cancer, neurological disorders, and other pathologies. A major source of reactive oxygen species (ROS) is a family of enzymes, NADPH oxidases (Nox), that catalyze electron transfer from NADPH to molecular oxygen to give ROS, such as superoxide ($O_2.^-$) and/or hydrogen peroxide ($H_2O_2$). Nox plays a crucial role in signaling cascades initiated by pro-inflammatory stimuli including hormones, vasoactive agents, and cytokines as well as mechanical stress. Members of this family include Nox1-5 as well as Duox1 and 2; in the human cardiovascular system, Nox1, 2, 4, and 5 isoforms are prevalent.

The major catalytic subunit of these Nox isozymes possesses six transmembrane domains with a cytosolic C-terminus containing NADPH- and FAD-binding domains. Specifically, Nox1, 2, and 4 are constitutively associated with membrane-bound $p22^{phox}$, the complex of which forms cytochrome b558. On the other hand, Nox5 does not require $p22^{phox}$ or cytosolic subunits but uniquely contains calcium-activating EF domains at its N-terminus. Furthermore, the Nox isozymes differ in requirements for specific cytosolic subunits for activation and organization. Nox1 associates with GTPase Rac1, cytosolic activator NoxA1, and cytosolic organizer NoxO1. Nox2 associates with Rac1 or Rac2 as well as cytosolic activator $p67^{phox}$ and cytosolic organizer $p47^{phox}$ while Nox4 requires no classical cytosolic subunits but is regulated by Poldip2 The result of activation of these enzymes is the generation of ROS in the form of $O_2.^-$ (Nox1, 2, 5) and $H_2O_2$ (Nox4). ROS production is mediated by electron transfer from NADPH in the cytosol to FAD to form $FADH_2$. Single electron transfer to heme groups on the transmembrane domains and subsequent transfer to molecular oxygen on the opposite side of the membrane forms $O_2.^-$, which can be converted to $H_2O_2$ by superoxide dismutase (SOD). Downstream effects of this ROS generation include changes in gene expression, cellular signaling, host defense and inflammation, and cell growth regulation. The inability of currently available agents to specifically inhibit a particular NADPH oxidase along with the combinative and varied expression of these isozymes in cells and tissue has made it difficult to assess their individual contributions to disease. Additionally, due to the wide distribution of the Nox enzymes in a variety of cells in the body as well as their beneficial role in signaling, nonspecific Nox inhibitors are likely to cause undesired effects in vivo.

Among the isoforms, Nox2 (aka $gp91^{phox}$, the first Nox isoform discovered) has been implicated in cardiovascular disease (CVD) processes including atherosclerosis, hypertension, ischemia reperfusion, cardiac hypertrophy, cardiomyopathy, stroke, and restenosis. In addition to CVDs, Nox2 has more recently been implicated in neurodegenerative diseases such as Huntington's, Alzheimer's, and Parkinson's diseases. Small molecules are the preferred therapeutic strategy for clinical use. However, due to the complex assembly and the high degree of homology among the various members of the Nox family, the development of isoform-specific inhibitors has proven challenging.

SUMMARY

Embodiments of nicotinamide adenine dinucleotide phosphate (NADPH) oxidase 2 (Nox2) inhibitors and pharmaceutical compositions comprising Nox2 inhibitors are disclosed. Methods of making and using the Nox2 inhibitors also are disclosed.

Embodiments of the disclosed compounds are bridged tetrahydroisoquinolines having a structure according to general formula I or a pharmaceutically acceptable salt thereof:

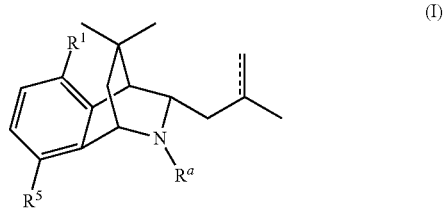

(I)

wherein "------" represents a single or double bond; $R^1$ is hydrogen, halogen, lower aliphatic, substituted or unsubstituted aryl, or substituted or unsubstituted heteroaryl; $R^a$ is hydrogen, $-CH_2R^2$, $R^3$, or $-SO_2R^4$; $R^2$ is lower aliphatic, substituted or unsubstituted aryl, or substituted or unsubstituted heteroaryl; $R^3$ is substituted or unsubstituted aryl, or substituted or unsubstituted heteroaryl; $R^4$ is lower aliphatic, or substituted or unsubstituted aryl; and $R^5$ is hydrogen, halogen, or lower aliphatic, provided that when $R^1$ is bromo or hydrogen, then $R^a$ is not hydrogen.

In any or all of the above embodiments, $R^1$ may be hydrogen, halogen, or substituted or unsubstituted aryl; $R^2$ may be lower alkyl, substituted or unsubstituted aryl, or substituted or unsubstituted heteroaryl; $R^4$ may be lower alkyl, or substituted or unsubstituted aryl; and $R^5$ may be hydrogen or halogen. In any or all of the above embodiments, $R^1$ may be halogen. In any or all of the above embodiments, $R^1$ may be bromo. In any or all of the above embodiments, $R^a$ may be $-CH_2R^2$ where $R^2$ is $C_1$-$C_5$ alkyl, substituted or unsubstituted $C_6$ aryl, or substituted or unsubstituted $C_3$-$C_5$ heteroaryl.

Exemplary compounds include, but are not limited to
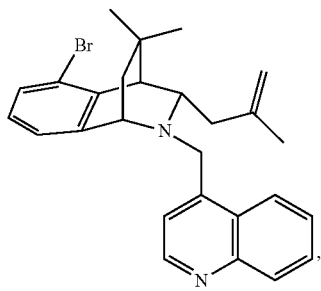,
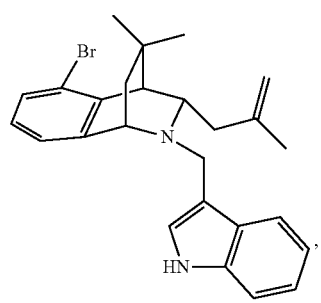,
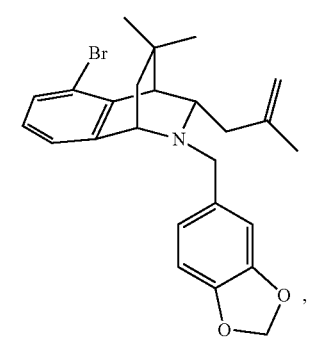,
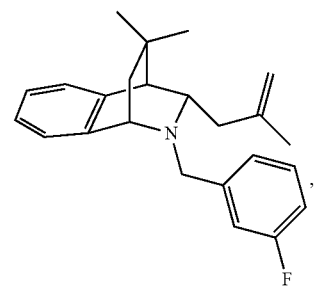,
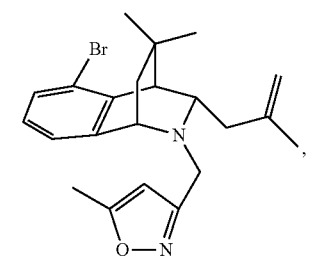,
-continued
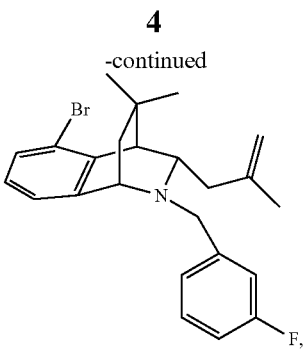,
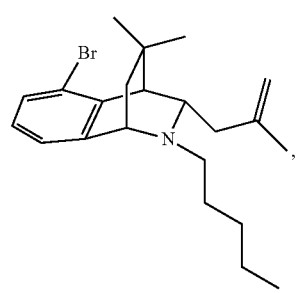,
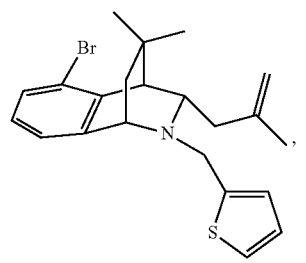,
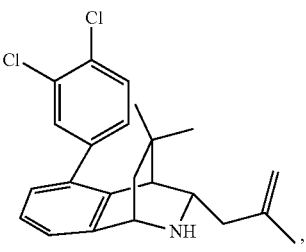,
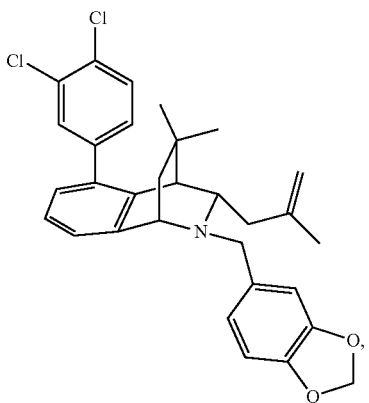, -continued

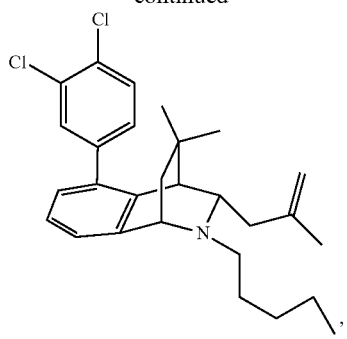

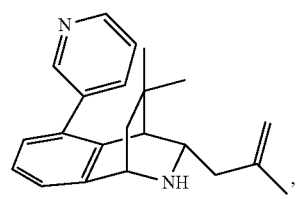

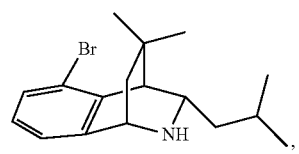

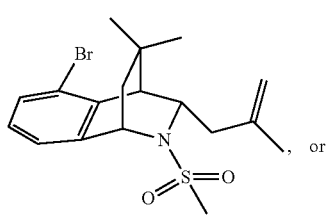, or

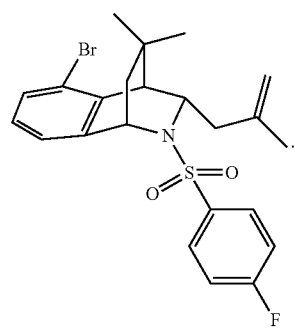

In some embodiments, the compound is

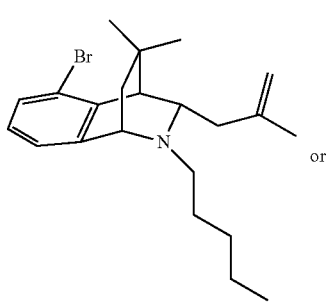 or

-continued

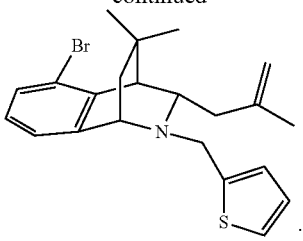

Pharmaceutical compositions include at least one compound according to any or all of the above embodiments or a pharmaceutically effective salt thereof, and at least one pharmaceutically acceptable additive.

In some embodiments, the pharmaceutical composition further includes an additional active agent. The additional active agent may be an antimicrobial agent, an anti-inflammatory agent, an anesthetic, an antihypertensive, a statin, a fibrate, a bile acid sequestrant, a plant sterol, an omega-3 fatty acid, an anti-platelet drug, an anti-thrombolytic, an antiarrhythmic, digoxin, an anticoagulant, an antipsychotic, an antianxiety drug, an antidepressant, an acetylcholinesterase inhibitor, an N-methyl-D-aspartate receptor antagonist, a dopamine agonist, a monoamine oxidase B inhibitor, a catechol o-methyltransferase inhibitor, a muscle relaxant, nicotinic acid, carbidopa-levodopa, hydrogen sulfide, cyclosporine, tetrabenazine, amantadine, digoxin, or any combination thereof.

Further disclosed herein is a method for selectively inhibiting Nox2 by contacting a cell with an effective amount of at least one compound according to any or all of the above embodiments or a pharmaceutically effective salt thereof. In some embodiments, the cell is contacted with the compound in vitro. In any or all of the above embodiments, contacting the cell with an effective amount of the compound may reduce a level of reactive oxygen species production in the cell compared to a cell not contacted with the compound.

Further disclosed herein is a method for treating or preventing a condition mediated by Nox2-related oxidative stress, comprising administering a therapeutically effective amount of a compound according to any or all of the above embodiments, or a pharmaceutically acceptable salt thereof, to a subject having, suspected of having, or at risk of developing, a condition mediated by Nox2 or reactive oxygen species produced by Nox2 activity.

In some embodiments, the condition is a cardiovascular disease, a neurodegenerative disease, diabetes, or cancer. Exemplary cardiovascular diseases include atherosclerosis, hypertension, ischemia reperfusion, cardiac hypertrophy, cardiomyopathy, stroke, restenosis, or any combination thereof. Exemplary neurodegenerative diseases include Huntington's disease, Alzheimer's disease, Parkinson's disease, or any combination thereof.

In any or all of the above embodiments, the method may further include identifying the subject as having, suspected of having, or at risk of developing a condition mediated by Nox2 by diagnosing the subject with a cardiovascular disease, a neurodegenerative disease, or cancer, or determining that the subject has one or more risk factors for a cardiovascular disease, a neurodegenerative disease, or cancer.

In any or all of the above embodiments, the method may further include administering to the subject (i) a therapeutically effective amount of an additional active agent, wherein the additional active agent is an antimicrobial agent, an anti-inflammatory agent, an anesthetic, an antihypertensive, a statin, a fibrate, a bile acid sequestrant, a plant sterol, an omega-3 fatty acid, an anti-platelet drug, an anti-thrombolytic, an antiarrhythmic, digoxin, an anticoagulant, an antipsychotic, an antianxiety drug, an antidepressant, an acetylcholinesterase inhibitor, an N-methyl-D-aspartate receptor antagonist, a dopamine agonist, a monoamine oxidase B inhibitor, a catechol o-methyltransferase inhibitor, a muscle relaxant, nicotinic acid, carbidopa-levodopa, hydrogen sulfide, cyclosporine, tetrabenazine, amantadine, digoxin, or any combination thereof; (ii) an adjunct therapy, wherein the adjunct therapy is stent placement, angioplasty, septal myectomy, ethanol ablation, an implantable cardioverter defibrillator, stem cell therapy, carotid endarterectomy, tissue plasminogen activator, brachytherapy, intracoronary radiation, deep brain stimulation, braces, physical therapy, occupational therapy, speech therapy, or any combination thereof; or (iii) a combination thereof. In the foregoing embodiments, the compound and the additional active agent, the adjunct therapy, or combination thereof may be administered to the subject simultaneously or sequentially in any order.

In any or all of the above embodiments of the method, the compound may have an $IC_{50}$ of ≤50 µM for inhibition of Nox2-mediated reactive oxygen species generation. In any or all of the above embodiments, the compound may selectively inhibit Nox2 activity compared to Nox1, Nox4, Nox5, and/or xanthine oxidase activity.

In any or all of the above embodiments of the method, the compound may be

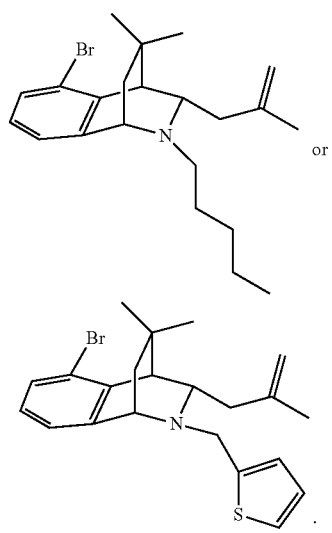 [SMILES: C=C(C)CC1C2c3c(Br)cccc3C(CC2(C)C)N1CCCCC ; C=C(C)CC1C2c3c(Br)cccc3C(CC2(C)C)N1Cc1cccs1]

The foregoing and other objects, features, and advantages of the invention will become more apparent from the following detailed description, which proceeds with reference to the accompanying figures.

DETAILED DESCRIPTION

Figure 1:
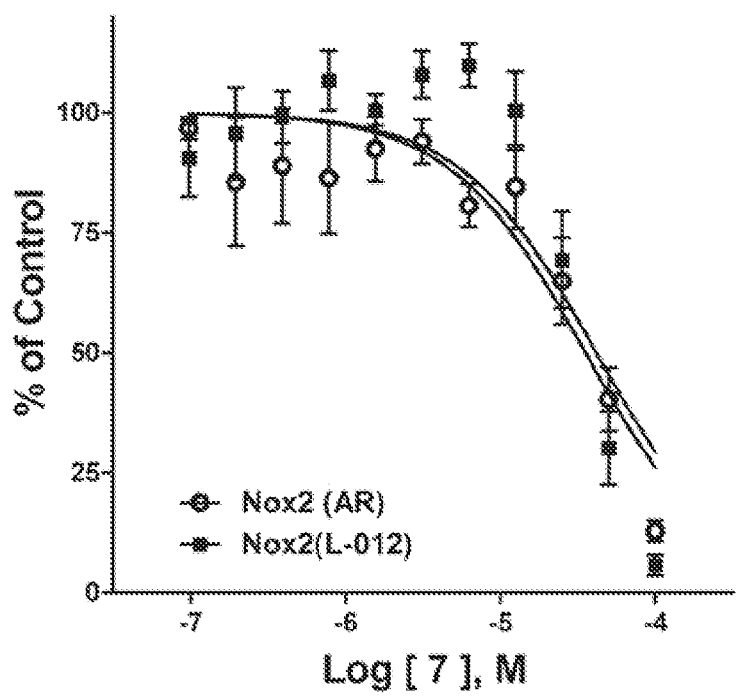
FIG. 1 is a graph showing concentration response testing of one embodiment of a Nox2 inhibitor, compound 7, in whole COS-Nox2 cells; the inhibitor was assayed with L-012 chemiluminescence (closed squares) and by Amplex® Red (open circles). Data are expressed as percent of vehicle control and represent the mean±SEM of 6 independent experiments.

Embodiments of bridged tetrahydroisoquinolines and methods for their use in selectively inhibiting nicotinamide adenine dinucleotide phosphate (NADPH) oxidase 2 (Nox2) are disclosed. The role of Nox2 in redox-signaling cascades effecting cellular dysfunction is well characterized. Selective Nox2 inhibitors may be useful for treating Nox2-related oxidative stress-mediated diseases. Exemplary diseases include, but are not limited to, cardiovascular disease (CVD) processes including atherosclerosis, hypertension, ischemia reperfusion, cardiomyopathy, cardiac hypertrophy, stroke, and restenosis, neurodegenerative diseases such as Huntington's, Alzheimer's, and Parkinson's diseases, and cancer. A selective inhibitor of Nox2 also may be useful for differentiating the Nox isoforms in a complex whole cell in vitro and/or in vivo environment. Certain embodiments of the disclosed Nox2 inhibitors interfere with the p47$^{phox}$-dependent activation process and/or reduce the oxidative burden in cell systems recapitulating human diseases.

I. TERMS AND DEFINITIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/ methods. When directly and explicitly distinguishing embodiments from discussed prior art, the embodiment numbers are not approximates unless the word "about" is recited.

In order to facilitate review of the various embodiments of the disclosure, the following explanations of specific terms are provided:

Alkyl: A hydrocarbon group having a saturated carbon chain. The chain may be cyclic, branched or unbranched. The term lower alkyl means the chain includes 1-10 carbon atoms. Unless otherwise specified, an alkyl group may be substituted or unsubstituted.

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). Exemplary aliphatic substituents include, for instance, amino, amide, sulfonamide, halo, cyano, carboxy, hydroxyl, mercapto, trifluoromethyl, alkyl, alkoxy, alkylthio, thioalkoxy, arylalkyl, heteroaryl, alkylamino, dialkylamino, or other functionality.

Aryl (sometimes referred to as "Ar"): A monovalent aromatic carbocyclic group of, unless specified otherwise, from 6 to 15 carbon atoms having a single ring (e.g., phenyl) or multiple condensed rings which condensed rings may or may not be aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic. Unless otherwise specified, an aryl group may be substituted or unsubstituted.

Effective amount or therapeutically effective dose: An amount sufficient to provide a beneficial, or therapeutic, effect to a subject or a given percentage of subjects.

Heteroaryl: A monovalent monocyclic or bicyclic aromatic radical of 5 to 10 ring atoms with each ring containing one, two, or three ring heteroatoms selected from N, O, or S, the remaining ring atoms being C. The aromatic radical is optionally fused to a phenyl or an optionally substituted heteroaryl ring or it is optionally substituted independently with one or more substituents, such as one or two substituents selected from alkyl, haloalkyl, heteroalkyl, aliphatic, heteroaliphatic, alkoxy, halo, cyano, nitro, aryl, optionally substituted heteroaryl, amino, monosubstituted amino, disubstituted amino, hydroxyamino, —OR (where R is hydrogen, haloalkyl, or optionally substituted phenyl), —S(O)$_n$R (where n is an integer from 0 to 2 and R is alkyl, haloalkyl, optionally substituted phenyl, amino, mono or disubstituted amino), —C(O)R (where R is hydrogen, alkyl, haloalkyl or optionally substituted phenyl), —COOR (where R is hydrogen, alkyl or optionally substituted phenyl), —C(O)N(R')R" (where R' and R" are independently selected from hydrogen, alkyl, haloalkyl, or optionally substituted phenyl). In specific examples, the term heteroaryl includes, but is not limited to pyridyl, pyrrolyl, thiophene, pyrazolyl, thiazolyl, imidazolyl, pyrimidinyl, thiadiazolyl, indolyl, carbazolyl, azaindolyl, benzofuranyl, benzimidazolyl, benzthiazolyl, quinoxalinyl, benzotriazolyl, benzisoxazolyl, purinyl, quinolinyl, isoquinolinyl, benzopyranyl, and derivatives thereof. Unless otherwise specified, heteroaryl group may be substituted or unsubstituted.

Nox2: Nicotinamide adenine dinucleotide phosphate (NADPH) oxidase 2.

Pharmaceutically acceptable salt: A biologically compatible salt of a compound that can be used as a drug, which salts are derived from a variety of organic and inorganic counter ions well known in the art.

ROS: Reactive oxygen species, e.g., superoxide, hydrogen peroxide.

Selectively inhibit or selectivity: As used herein, the terms "selectively inhibit" and "selectivity" refer to a compound's ability to inhibit a particular NADPH oxidase isoform while being inactive or substantially less active against other NADPH oxidases.

SOD: Superoxide dismutase.

Subject: An animal or human subjected to a treatment, observation or experiment.

Substituent: An atom or group of atoms that replaces another atom in a molecule as the result of a reaction. The term "substituent" typically refers to an atom or group of atoms that replaces a hydrogen atom on a parent hydrocarbon chain or ring.

Substituted: A fundamental compound, such as an aryl, heteroaryl, or alkyl compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a hydrocarbon may have a substituent bonded thereto, such as one or more halogens, an aryl group, a cyclic group, a heteroaryl group or a heterocyclic group.

Treating or treatment: With respect to disease, either term includes (1) preventing the disease, e.g., causing the clinical symptoms of the disease not to develop in a human or non-human animal that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

II. NOX2 INHIBITORS

The disclosed Nox2 inhibitors are bridged tetrahydroisoquinolines, such as (1SR,4RS)-3,3-dimethyl-1,2,3,4-tetrahydro-1,4-(epiminomethano)napthalenes. Embodiments of the disclosed Nox 2 inhibitors have a structure according to general formula I:

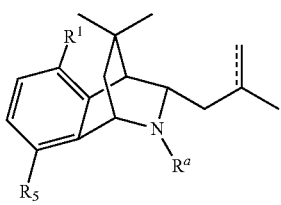

(I)

wherein "------" represents a single or double bond; $R^1$ is hydrogen, halogen, lower aliphatic, such as lower alkyl, substituted or unsubstituted aryl, or substituted or unsubstituted heteroaryl; $R^a$ is hydrogen, —$CH_2R^2$, $R^3$, or —$SO_2R^4$; $R^2$ is lower aliphatic, such as lower alkyl, substituted or unsubstituted aryl, or substituted or unsubstituted heteroaryl; $R^3$ is substituted or unsubstituted aryl, or substituted or unsubstituted heteroaryl; $R^4$ is lower aliphatic, such as lower alkyl, or substituted or unsubstituted aryl; and $R^5$ is hydrogen, halogen, or lower aliphatic, such as lower alkyl. In some embodiments, when $R^1$ is bromo or hydrogen, then $R^a$ is not hydrogen.

In some embodiments, $R^1$ is hydrogen, halogen, or substituted or unsubstituted aryl; $R^2$ is lower alkyl, substituted or unsubstituted aryl, or substituted or unsubstituted heteroaryl; $R^4$ is lower alkyl, or substituted or unsubstituted aryl, and $R^5$ is hydrogen or halogen. In one independent embodiment, $R^1$ is halogen, e.g., bromo.

In some embodiments, $R^1$ is halogen or substituted or unsubstituted aryl. In one independent embodiment, $R^1$ is halogen. For example, $R^1$ may be bromo. In another independent embodiment, $R^1$ is substituted or unsubstituted aryl or heteroaryl. For example, $R^1$ may be haloaryl or heteroaryl. In one example, $R^1$ is 3,4-dichlorophenyl. In another example, $R^1$ is 3-pyridyl.

In some embodiments, $R^a$ is hydrogen, —$CH_2R^2$, or $R^3$. In one independent embodiment, $R^a$ is hydrogen. In one example, $R^a$ is hydrogen and $R^1$ is substituted or unsubstituted aryl or heteroaryl.

In another independent embodiment, $R^a$ is —$CH_2R^2$, where $R^2$ is substituted or unsubstituted lower alkyl, substituted or unsubstituted aryl, or substituted or unsubstituted heteroaryl. In one example, $R^2$ is lower alkyl, such as $C_1$-$C_5$ alkyl or $C_1$-$C_3$ alkyl. In another example, $R^2$ is substituted or unsubstituted aryl or heteroaryl, e.g., $C_6$ aryl or $C_3$-$C_5$ heteroaryl. In some instances, $R^2$ is haloaryl, such as 3-halophenyl, or heteroaryl, such as thiophene, oxazole, indole, quinoline, or benzodioxole (e.g., 1,3-benzodioxole).

In yet another independent embodiment, $R^a$ is —$SO_2R^4$, where $R^4$ is lower alkyl or substituted or unsubstituted aryl. In one example, $R^4$ is lower alkyl, such as $C_1$-$C_5$ alkyl, or $C_1$-$C_3$ alkyl. In another example, $R^4$ is aryl, such as haloaryl.

In any of the foregoing embodiments, $R^5$ may be hydrogen.

Several exemplary compounds are shown in Table 1.

TABLE 1

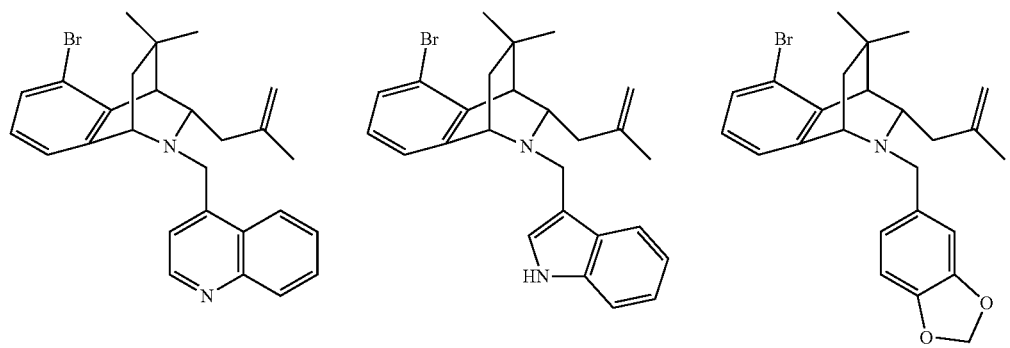

TABLE 1-continued
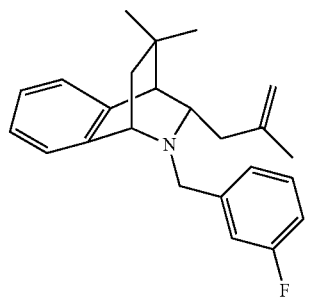 [SMILES: C=C(C)CC1C2c3ccccc3C(CC2(C)C)N1Cc1cccc(F)c1] 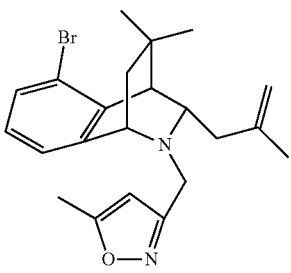 [SMILES: C=C(C)CC1C2c3c(Br)cccc3C(CC2(C)C)N1Cc1cc(C)on1] 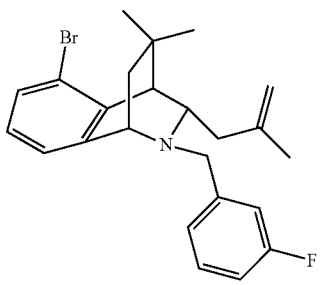 [SMILES: C=C(C)CC1C2c3c(Br)cccc3C(CC2(C)C)N1Cc1cccc(F)c1]
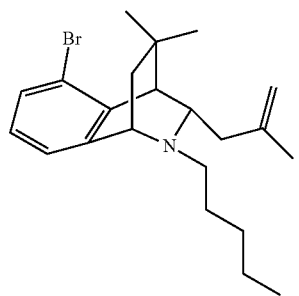 [SMILES: C=C(C)CC1C2c3c(Br)cccc3C(CC2(C)C)N1CCCCC] 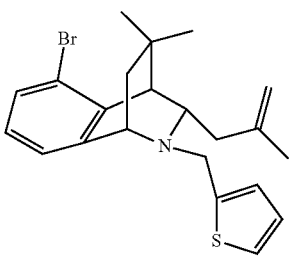 [SMILES: C=C(C)CC1C2c3c(Br)cccc3C(CC2(C)C)N1Cc1cccs1] 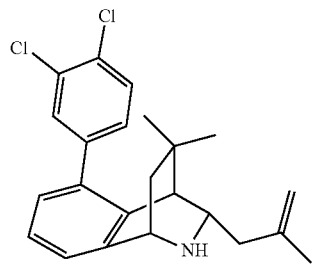 [SMILES: C=C(C)CC1NC2CC(C)(C)C1c1c(-c3ccc(Cl)c(Cl)c3)cccc12]
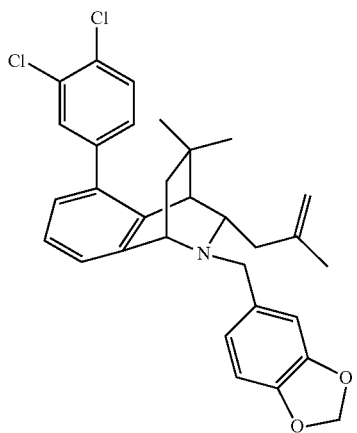 [SMILES: C=C(C)CC1C2c3c(-c4ccc(Cl)c(Cl)c4)cccc3C(CC2(C)C)N1Cc1ccc2c(c1)OCO2] 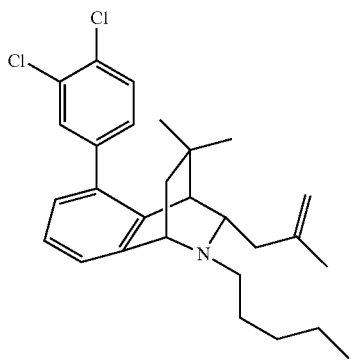 [SMILES: C=C(C)CC1C2c3c(-c4ccc(Cl)c(Cl)c4)cccc3C(CC2(C)C)N1CCCCC] 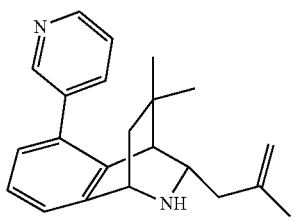 [SMILES: C=C(C)CC1NC2CC(C)(C)C1c1c(-c3cccnc3)cccc12]
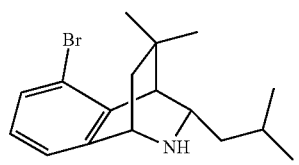 [SMILES: CC(C)CC1NC2CC(C)(C)C1c1c(Br)cccc12] 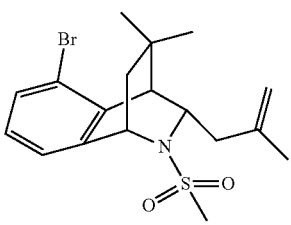 [SMILES: C=C(C)CC1C2c3c(Br)cccc3C(CC2(C)C)N1S(C)(=O)=O] 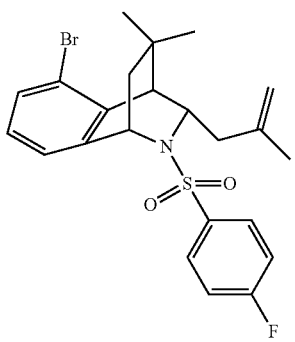 [SMILES: C=C(C)CC1C2c3c(Br)cccc3C(CC2(C)C)N1S(=O)(=O)c1ccc(F)cc1]

In certain examples, the Nox2 inhibitor is

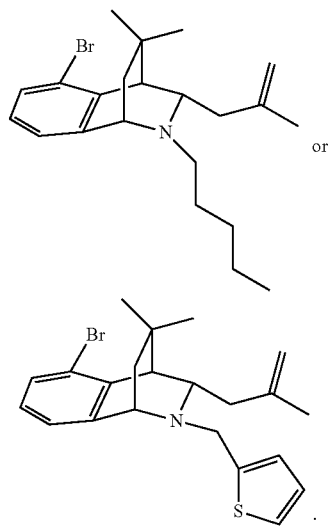 [SMILES: C=C(C)CC1C2c3c(Br)cccc3C(CC2(C)C)N1CCCCC ; C=C(C)CC1C2c3c(Br)cccc3C(CC2(C)C)N1Cc1cccs1]

In one independent embodiment, the Nox2 inhibitor is selective for Nox2 over at least one of Nox1, Nox4, and Nox5. In some example, the Nox2 inhibitor is selective for Nox2 over Nox1, Nox4, and Nox5. In another independent embodiment, the Nox2 inhibitor has little or no inhibitory effect on xanthine oxidase (XO), which also produces ROS.

In one independent embodiment, the Nox2 inhibitor has an $IC_{50}$ of ≤50 μM for inhibition of Nox2-mediated reactive oxygen species generation, such as an $IC_{50}$ of 25 nM to 50 μM, 100 nM to 50 μM, 1-50 μM, 10-40 μM, or 25-40 μM. The $IC_{50}$ may be lower, e.g., 100- to 1000-fold lower, in a cell-free system.

III. COMPOUND SYNTHESIS

Embodiments of the disclosed bridged tetrahydroisoquinoline derivatives may be synthesized in 2-3 steps from isoquinolines. Compounds 7 and 8 were prepared through a double allylation and carbometallation-cyclization sequence from 5-bromoisoquinoline and isoquinoline, respectively, as shown in Scheme 1. The bridged cyclic structure of compound 8 was confirmed by comparison of the $^1$H and $^{13}$C NMR spectra to those reported for compound 8 (Bubnov et al., *Pure Appl. Chem.* 2000, 72:1641-1644. Compounds 7 and 8 were also used as building blocks for the generation of a series of bridged analogs. Tertiary amines, compounds 11a-h, were formed via reductive amination of compound 7 and compound 8 with a variety of aldehydes (Scheme 1).

Scheme 1

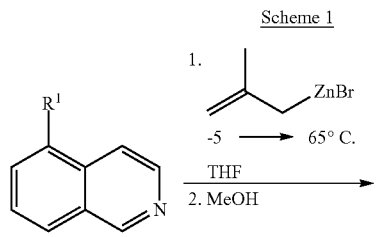

10a: $R^1$ = Br
10b: $R^1$ = H

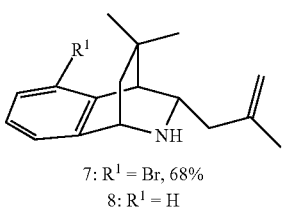

7: $R^1$ = Br, 68%
8: $R^1$ = H 11a-h

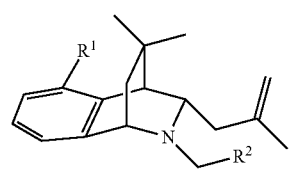

11a: $R^1$ = H, $R^2$ = m-F—Ph, 63%
11b: $R^1$ = Br, $R^2$ = 4-quinoline, 69%
11c: $R^1$ = Br, $R^2$ = 3-indole, 27%
11d: $R^1$ = Br, $R^2$ = 5-benzo[1,3]dioxole, 70%
11e: $R^1$ = Br, $R^2$ = 3-(5-methylisozazole), 27%
11f: $R^1$ = Br, $R^2$ = m-F—Ph, 39%
11g: $R^1$ = Br, $R^2$ = n-$C_4H_9$, 72%
11h: $R^1$ = Br, $R^2$ = 2-thiophene, 67%

An additional series of biaryl analogs was synthesized to evaluate functional tolerance at the 5-position of the isoquinoline. These compounds were prepared by Suzuki-Miyaura cross coupling with aryl boronic acids (Scheme 2). Both the secondary amines (prepared in Scheme 1) and the tertiary amines 11d and 11g were coupled to give the C5-aryl-substituted tetrahydroisoquinolines 12a-d.

Scheme 2

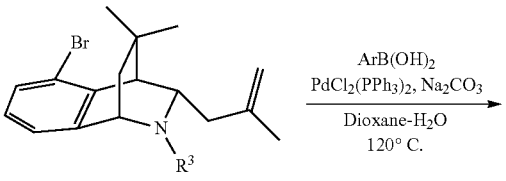

7, 11d, 11g

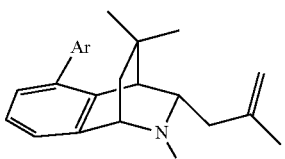

12a-d

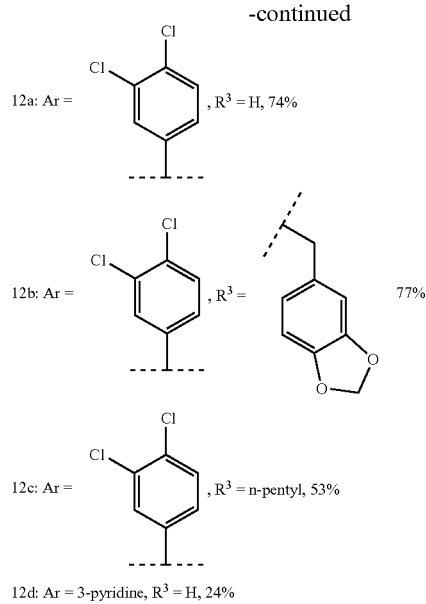

12a: Ar = [3,4-dichlorophenyl], R³ = H, 74%

12b: Ar = [3,4-dichlorophenyl], R³ = [benzodioxole-methyl], 77%

12c: Ar = [3,4-dichlorophenyl], R³ = n-pentyl, 53%

12d: Ar = 3-pyridine, R³ = H, 24%

The disubstituted alkene was reduced in the presence of the aryl bromide using 5% rhodium on carbon to form compound 13 in 91% yield (Scheme 3). An alkyl and an aryl sulfonamide, 14a and 14b, were prepared by reaction with the corresponding sulfonyl chlorides.

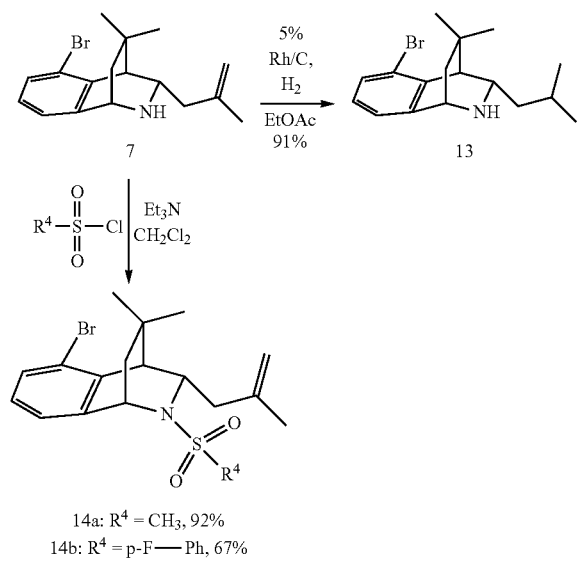

Scheme 3

14a: R⁴ = CH₃, 92%
14b: R⁴ = p-F—Ph, 67%

IV. METHODS OF USE

A. Treatment or Prevention of Conditions Mediated by Nox2

Embodiments of the disclosed NADPH oxidase 2 inhibitors are useful for treating conditions mediated by Nox2-related oxidative stress, including cardiovascular disease processes, neurodegenerative diseases, and/or cancer. Exemplary cardiovascular disease conditions include, but are not limited to, atherosclerosis, hypertension, ischemia reperfusion, cardiac hypertrophy, cardiomyopathy (e.g., diabetes-induced cardiomyopathy), stroke, restenosis, or any combination thereof. Exemplary neurodegenerative diseases include, but are not limited to, Huntington's disease, Alzheimer's disease, Parkinson's disease, or any combination thereof. Embodiments of the disclosed Nox2 inhibitors also may be useful for treating drug-induced cardiotoxicity resulting from increased ROS production, such as doxorubicin-induced cardiotoxicity.

In one independent embodiment, Nox2 is inhibited by contacting a cell with an effective amount of a compound according to general formula I or a pharmaceutically acceptable salt thereof. In some examples, $R^1$ is halogen, or substituted or unsubstituted aryl, and $R^a$ is hydrogen, —$CH_2R^2$, or $R^3$, wherein $R^2$ and $R^3$ are as described above. In certain examples, $R^1$ is bromo, $R^a$ is —$CH_2R^2$ where $R^2$ is n-butyl or 2-thiophene, and $R^5$ is hydrogen. The cell may be contacted with the compound in an in vitro or in vivo environment.

In another independent embodiment, a therapeutically effective amount of a compound according to general formula I, or a pharmaceutically acceptable salt thereof, is administered to a subject having, suspected of having, or at risk of developing, a condition mediated by Nox2 and/or ROS produced by Nox2 activity. In some examples, $R^1$ is halogen, or substituted or unsubstituted aryl, and $R^a$ is hydrogen, —$CH_2R^2$, or $R^3$, wherein $R^2$ and $R^3$ are as described above. In certain examples, $R^1$ is bromo, $R^a$ is —$CH_2R^2$ where $R^2$ is n-butyl or 2-thiophene, and $R^5$ is hydrogen.

The Nox2 inhibitors described herein, or compositions thereof, will generally be used in an amount effective to achieve the intended result, for example in an amount effective to treat a condition mediated by Nox2. By therapeutic benefit is meant eradication or amelioration of one or more of the symptoms associated with the underlying disorder such that the subject reports an improvement in feeling or condition, notwithstanding that the subject may still be afflicted with the underlying disorder.

The amount of compound administered will depend upon a variety of factors, including, for example, the particular condition being treated, the mode of administration, the severity of the condition being treated and the age and weight of the patient, the bioavailability of the particular active compound, etc. Determination of an effective dosage is well within the capabilities of those skilled in the art. A skilled practitioner will be able to determine the optimal dose for a particular individual. Effective dosages may be estimated initially from in vitro or in vivo assays. For example, an initial dosage for use in animals may be formulated to achieve a circulating blood or serum concentration of active compound that is at or above an $EC_{50}$ of the particular compound as measured in an in vitro assay or an in vivo assay. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, latest edition, Pergamon Press, and the references cited therein.

Embodiments of the disclosed Nox2 inhibitors may be administered by oral, parenteral (for example, intramuscular, intraperitoneal, intravenous, ICV, intracisternal injection or infusion, subcutaneous injection, or implant), by inhalation spray, nasal, vaginal, rectal, sublingual, urethral (for example, urethral suppository) or topical routes of administration (for example, gel, ointment, cream, aerosol, etc.)

and may be formulated, alone or together, in suitable dosage unit formulations containing conventional non-toxic pharmaceutically acceptable carriers, adjuvants, excipients and vehicles appropriate for each route of administration. In addition to the treatment of warm-blooded animals such as mice, rats, horses, cattle, sheep, dogs, cats, monkeys, etc., the compounds described herein may be effective in humans.

Pharmaceutical compositions for administration to a subject can include at least one further pharmaceutically acceptable additive such as carriers, thickeners, diluents, buffers, preservatives, surface active agents and the like in addition to the Nox2 inhibitor. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds disclosed herein.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed Nox2 inhibitor. Pharmaceutically acceptable salts include those derived from pharmaceutically acceptable inorganic or organic bases and acids. For example, when $R^a$ is hydrogen, the compound might be an ammonium salt.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the Nox2 inhibitor can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of 0.3 to 3.0, such as 0.5 to 2.0, or 0.8 to 1.7.

The Nox2 inhibitor can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The Nox2 inhibitor can be combined with the base or vehicle according to a variety of methods, and release of the compound can be by diffusion, disintegration of the vehicle, or associated formation of water channels. In some circumstances, the Nox2 inhibitor is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the Nox2 inhibitor can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the Nox2 inhibitor can be brought about by including in the composition an agent which delays absorption, for example, monostearate salts and gelatin.

In certain embodiments, the Nox2 inhibitor can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the Nox2 inhibitor and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly($\epsilon$-caprolactone), poly($\epsilon$-caprolactone-CO-lactic acid), poly($\epsilon$-caprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917, 893), lactic acid-glycolic acid copolymers useful in making microcapsules and other formulations (U.S. Pat. Nos. 4,677, 191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the Nox2 inhibitor can be delivered to a subject in a manner consistent with conventional methodologies associated with management of the disorder for which treatment or prevention is sought. In accordance with the disclosure herein, a prophylactically or therapeutically effective amount of the Nox2 inhibitor is administered to a subject in need of such treatment for a time and under conditions sufficient to inhibit, and/or ameliorate a selected disease or condition or one or more symptom(s) thereof.

The administration of the Nox2 inhibitor of the disclosure can be for either prophylactic or therapeutic purpose. When provided prophylactically, the Nox2 inhibitor is provided in advance of any symptom. The prophylactic administration of the Nox2 inhibitor serves to inhibit or ameliorate any subsequent disease process. When provided therapeutically, the Nox2 inhibitor is provided at (or shortly after) the onset of a symptom of disease.

For prophylactic and therapeutic purposes, the Nox2 inhibitor can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the Nox2 inhibitor can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the Nox2 inhibitor (for example, amounts that are effective to elicit a desired reduction in Nox2 activity and/or ROS generation, and/or to alleviate one or more symptoms of a targeted disease).

The actual dosage of the Nox2 inhibitor will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is 0.01 mg/kg body weight to 50 mg/kg body weight, such as 0.01 mg/kg to 20 mg/kg, 0.05 mg/kg to 5 mg/kg body weight, or 0.2 mg/kg to 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intra-nasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The Nox2 inhibitors disclosed herein may be co-administered with an additional therapeutic or active agent. Such agents include, but are not limited to, antimicrobial agents, anti-inflammatory agents, anesthetics, antihypertensives (e.g., adrenergic receptor antagonists (alpha blockers and/or beta blockers), aldosterone receptor antagonists, alpha 2 agonists, angiotensin-converting enzyme (ACE) inhibitors, angiotensin II receptor antagonists, benzodiazepines, calcium channel blockers, diuretics, endothelin receptor blockers, renin inhibitors, vasodilators), statins, fibrates, nicotinic acid, bile acid sequestrants (cholestyramine, colestipol, colesevelam), plant sterols, omega-3 fatty acids, anti-platelet drugs (e.g., aspirin), anti-thrombolytics, antiarrhythmics, digoxin, anticoagulants, hydrogen sulfide, cyclosporine, tetrabenazine, antipsychotic drugs (e.g., haloperidol, clozapine), antiseizure drugs (e.g., clonazepam), antianxiety drugs (e.g., diazepam), antidepressants, acetylcholinesterase inhibitors (tacrine, rivastigmine, galantamine, donepezil), NMDA (N-methyl-D-aspartate) receptor antagonists, carbidopa-levodopa, dopamine agonists, MAO-B (monoamine oxidase B) inhibitors, catechol o-methyltransferase inhibitors, amantadine, muscle relaxants, and combinations thereof. The Nox2 inhibitor also may be co-administered with adjunct therapies, such as stent placement (e.g., a drug-eluting stent), angioplasty, septal myectomy, ethanol ablation, implantable cardioverter defibrillators, stem cell therapy, carotid endarterectomy, tissue plasminogen activator, brachytherapy, intracoronary radiation, deep brain stimulation, braces, physical therapy, occupational therapy, speech therapy, or combinations thereof. Co-administration may be performed simultaneously or sequentially.

B. An Experimental Tool for Studying Nox2

Independent of the therapeutic potential for conditions mediated by Nox2-related oxidative stress, the Nox2 inhibitors described herein are an important experimental tool for studying the basic properties of Nox2. For example, the disclosed compounds could be used to explore Nox2 protective mutations and/or deletions in the inhibitor binding regions of Nox2. Embodiments of the disclosed Nox2 inhibitors also could be useful as probes to more fully discern the biological role of Nox2 as compared to other Nox isoforms and/or could potentially serve as a platform for developing additional therapeutic agents for treatment of Nox-2 related diseases.

V. KITS

The instant disclosure also includes kits, packages and multi-container units containing the herein described pharmaceutical compositions, active ingredients, and/or means for administering the same for use in the prevention and treatment of diseases and other conditions in mammalian subjects. The Nox2 inhibitor may be formulated in a pharmaceutical preparation for delivery to a subject. The Nox2 inhibitor is optionally contained in a bulk dispensing container or unit or multi-unit dosage form. Optional dispensing means can be provided, for example a pulmonary or intra-nasal spray applicator. Packaging materials optionally include a label or instruction indicating for what treatment purposes and/or in what manner the pharmaceutical agent packaged therewith can be used.

VI. EXAMPLES

Example 1

Compound Syntheses and Characterization

General Chemistry Methods:

All moisture sensitive reactions were performed using syringe-septum techniques under an atmosphere of either dry $N_2$ or dry argon unless otherwise noted. All glassware used in moisture sensitive reactions was flame-dried or oven dried at 136° C. overnight and cooled in a desiccator prior to use. All chemicals were purchased from commercial suppliers and unless otherwise noted were used as received. All the microwave reactions were performed using a Biotage® Initiator microwave reactor. Tetrahydrofuran (THF) was dried by distillation over sodium/benzophenone under an argon atmosphere. Dry dichloromethane ($CH_2Cl_2$), dichloroethane ($C_2H_4Cl_2$), and ethyl acetate (EtOAc) were obtained by distillation over calcium hydride under an argon atmosphere. Deuterated chloroform ($CDCl_3$) was filtered through an alumina plug prior to use. Reactions were monitored by TLC analysis (pre-coated silica gel 60 $F_{254}$ plates, 250 μm layer thickness) and visualized by using UV lamp (254 nm) and/or a potassium permanganate solution (3 g of $KMnO_4$ and 4 g of $K_2CO_3$ in 4 mL of 5% NaOH solution and 200 mL of $H_2O$). Flash column chromatography was performed with 40-63 μm silica gel ($SiO_2$, Silicycle). Infrared spectra were recorded on a Smiths IdentifyIR ATR spectrometer or a Perkin Elmer Spectrum 100 FT-IR spectrometer using the Universal ATR Sampling Accessory. All NMR data was collected at room temperature in $CDCl_3$ on a 300, 400 or 500 MHz Bruker instrument. Chemical shifts (δ) are reported in parts per million (ppm) with internal $CHCl_3$ (δ 7.26 ppm for $^1H$ and 77.23 ppm for $^{13}C$). $^1H$ NMR data are reported as follows: chemical shift, multiplicity (s=singlet, bs=broad singlet, d=doublet, t=triplet, q=quartet, m=multiplet, bm=broad multiplet, dd=doublet of doublets, dt=doublet of triplets, td=triplet of doublets, qd=quartet of doublets, sep=septet, app t=apparent triplet), integration, and coupling constant(s) (J) in Hertz (Hz). $^{13}C$ NMR spectra were measured using a protondecoupled pulse sequence. Final products were >95% purity as analyzed by reverse-phase HPLC (ACCELA PDA detector, 1250 pump, Waters XTerra® MS 3.5 μm C-18 50×2 mm column, 0.5 mL/min, $CH_3CN$, $H_2O$ and 0.1% formic acid) with UV (210, 220 and 254 nm), ELSD (Agilent Technologies 385-ELSD, nebulizer 45° C., evaporator 45° C., $N_2$ flow 1.80 SLM), and MS detection using a Thermo Scientific Exactive Orbitrap LC-MS (HESI positive).

Syntheses and Characterization:

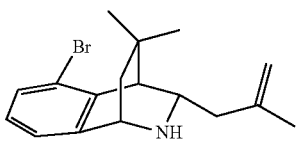 [SMILES: C=C(C)CC1NC2CC(C)(C)C1c1c(Br)cccc12]

(±)-(1S,4R,9S)-5-Bromo-3,3-dimethyl-9-(2-methylallyl)-1,2,3,4-tetrahydro-1,4-(epimino-methano)-naphthalene (7)

To a stirred solution of 5-bromoisoquinoline (0.1 g, 0.5 mmol) in anhydrous THF (0.2 mL) was added methallylzinc bromide in THF (2 mL, 1.0 M) dropwise at 0° C. and the resulting solution was stirred for 10 min. The reaction mixture was warmed to room temperature, heated to 70° C. for 4.5 h, cooled to room temperature and further cooled to −10° C. The reaction was quenched by dropwise addition of MeOH (0.1 mL). The reaction mixture was poured onto ice water (20 mL) and extracted with $Et_2O$ (2×15 mL). The combined organic portion was dried ($Na_2SO_4$), concentrated, and the crude product was purified by chromatography on neutral $Al_2O_3$ (1:1, hexanes:EtOAc followed by 7:93, $CH_3OH:CH_2Cl_2$) to give 7 (105 mg, 68%, 97% purity by ELSD) as a colorless oil: IR (neat) 3073, 2934, 1647, 1564, 1451, 1369, 1330, 1310, 1273, 1177, 1142, 1117, 1073, 965, 891, 822, 767, 742, 702, 688 $cm^{-1}$; $^1H$ NMR (300 MHz, $CDCl_3$) δ 7.43 (dd, J=1.3, 7.8 Hz, 1H), 7.10-7.00 (m, 2H), 4.73 (s, 1H), 4.55 (s, 1H), 3.85 (t, J=2.9 Hz, 1H), 3.74 (ddd, J=1.6, 5.2, 8.7 Hz, 1H), 2.94 (s, 1H), 1.86-1.79 (m, 2H), 1.71 (s, 3H), 1.34-1.18 (m, 5H), 0.62 (s, 3H); $^{13}C$ NMR (75 MHz, $CDCl_3$) δ 144.4, 142.2, 139.3, 129.9, 127.7, 123.7, 120.9, 113.1, 52.7, 49.7, 48.8, 42.5, 32.4, 30.9, 28.8, 22.4; HRMS (ESI) m/z calcd for $C_{17}H_{23}BrN$ $(M+H)^+$ 320.1008. found 320.1001.

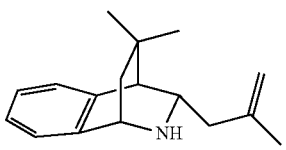

(±)-(1S,4R,9S)-3,3-Dimethyl-9-(2-methylallyl)-1,2,3,4-tetrahydro-1,4-(epiminomethano)-naphthalene (8)

Isoquinoline (0.1 g, 0.8 mmol) was charged with a solution of methallylzinc bromide (2.50 mL, 1.12 M in THF, 2.47 mmol) at 0° C. and stirred for 10 min. After warming the reaction mixture to room temperature, it was heated to 70° C. for 1 h, then cooled to room temperature and further cooled to −10° C. The reaction was quenched by dropwise addition of MeOH (0.2 mL). To this solution was added 6 N NaOH (20 mL) and the organic layer was separated, dried ($Na_2SO_4$), and purified by chromatography on neutral $Al_2O_3$ (1:1, hexanes:EtOAc followed by 7:93, $CH_3OH:CH_2Cl_2$) to give 8 (50 mg, 27%) as a colorless oil. The $^1H$ NMR matched that of the previously reported compound (Bubnov et al., *Russ. Chem, Bull.*, 2001, 50, 2172).

General Method A: Reductive Amination.

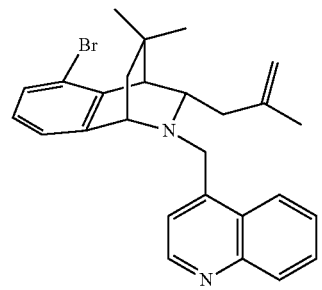 [SMILES: C=C(C)CC1C2c3c(Br)cccc3C(CC2(C)C)N1Cc1ccnc2ccccc12]

(±)-(1S,4R,9S)-5-Bromo-3,3-dimethyl-9-(2-methylallyl)-10-(quinolin-4-ylmethyl)-1,2,3,4-tetrahydro-1,4-(epiminomethano)naphthalene (11b)

To a stirred solution of 7 (0.04 g, 0.1 mmol), 4-quinoline carboxaldehyde (22 mg, 0.14 mmol) and acetic acid (7.0 mL, 0.12 mmol) in dichloroethane (1.2 mL) was added sodium triacetoxyborohydride (53 mg, 0.25 mmol). The reaction mixture was stirred for 48 h under argon, diluted with $CH_2Cl_2$ (10 mL), and treated with a saturated solution of $NaHCO_3$ (10 mL). The organic layer was washed with $H_2O$ (10 mL) and the combined organic layer was dried ($Na_2SO_4$) and concentrated. The crude product was purified by chromatography on $SiO_2$ (95:5, hexanes:EtOAc) to give 11b (0.04 g, 69%, 99% purity by ELSD) as a colorless oil: IR (neat) 3068, 2958, 1590, 1567, 1506, 1452, 1357, 1189, 908, 760, 731 $cm^{-1}$; $^1H$ NMR (400 MHz, $CDCl_3$) δ 8.85 (d, J=4.3 Hz, 1H), 8.21 (dd, J=1.1, 8.5 Hz, 1H), 8.12 (dd, J=0.9, 8.5 Hz, 1H), 7.69 (ddd, J=1.4, 6.9, 8.3 Hz, 1H), 7.52-7.48 (m, 2H), 7.43 (dd, J=0.9, 8.1 Hz, 1H), 7.04 (app t, J=7.6 Hz, 1H), 6.88 (d, J=7.2 Hz, 1H), 4.78 (d, J=4.8 Hz, 1H), 4.46 (d, J=14.9 Hz, 1H), 4.23 (d, J=15.0 Hz, 1H), 3.54 (t, J=2.5 Hz, 1H), 3.38 (ddd, J=1.7, 4.4, 9.0 Hz, 1H), 3.05 (d, J=1.5 Hz, 1H), 2.12 (dd, J=2.6, 13.7 Hz, 1H), 1.79 (dd, J=4.3, 14.3 Hz, 1H), 1.82-1.67 (m, 1H), 1.73 (s, 3H), 1.41 (s, 3H), 1.00 (dd, J=2.5, 13.6 Hz, 1H), 0.6 (s, 3H); $^{13}C$ NMR (100 MHz, $CDCl_3$) δ 150.6, 148.4, 145.9, 144.1, 142.5, 139.9, 130.3, 130.2, 129.3, 127.7, 127.6, 126.5, 124.0, 123.3, 121.3, 121.0, 113.2, 57.5, 55.8, 53.3, 49.4, 44.4, 35.2, 33.0, 31.0, 28.5, 22.9; HRMS (ESI) m/z calcd for $C_{27}H_{30}O_2BrN_2$ $(M+H)^+$ 461.1587, found 461.1581.

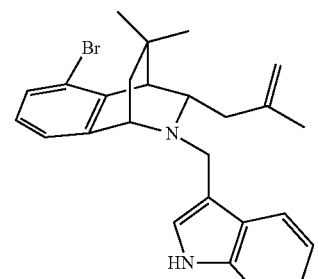

(±)-(1S,4R,9S)-10-((1H-Indol-3-yl)methyl)-5-bromo-3,3-dimethyl-9-(2-methylallyl)-1,2,3,4-tetrahydro-1,4-(epiminomethano)naphthalene (11c)

According to General Method A, 7 (0.04 g, 0.1 mmol) was converted to pale yellow oily 11c (15 mg, 27%, 98% purity by ELSD): IR (neat) 3411, 2926, 1727, 1567, 1455, 1353, 1264, 1189, 1091, 1044, 1010, 930, 893, 807, 772, 734 cm$^{-1}$; $^1$H NMR (400 MHz, CDCl$_3$) δ 8.04 (s, 1H), 7.71 (d, J=8.0 Hz, 1H), 7.37 (dd, J=8.2, 12.8 Hz, 2H), 7.21-7.15 (m, 2H), 7.07 (t, J=7.5 Hz, 1H), 6.99 (t, J=7.7 Hz, 1H), 6.83 (d, J=7.0 Hz, 1H), 4.81 (d, J=8.1 Hz, 2H), 4.09 (s, 2H), 3.75 (t, J=2.7 Hz, 1H), 3.26 (dd, J=3.5, 9.9 Hz, 1H), 3.0 (s, 1H), 2.15 (dd, J=2.4, 13.6 Hz, 1H), 1.89 (dd, J=3.5, 14.4 Hz, 1H), 1.75-1.65 (m, 1H), 1.69 (s, 3H), 1.37 (s, 3H), 0.92 (dd, J=2.3, 13.6 Hz, 1H), 0.57 (s, 3H); $^{13}$C NMR (100 MHz, CDCl$_3$) δ 144.8, 143.1, 140.3, 136.6, 130.0, 127.8, 127.5, 123.4, 123.2, 122.3, 121.6, 120.2, 119.6, 114.6, 113.0, 111.1, 57.1, 55.1, 49.3, 47.5, 44.5, 34.7, 33.0, 31.1, 29.9, 28.4, 22.9; HRMS (ESI) m/z calcd for C$_{26}$H$_{30}$BrN$_2$ (M+H)$^+$ 449.1587, found 449.1575.

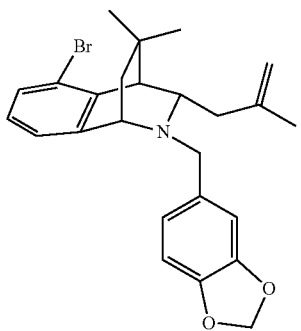 [SMILES: C=C(C)CC1C2c3c(Br)cccc3C(CC2(C)C)N1Cc1ccc2c(c1)OCO2]

(±)-(1S,4R,9S)-10-(Benzo[d][1,3]dioxol-5-ylmethyl)-5-bromo-3,3-dimethyl-9-(2-methylallyl)-1,2,3,4-tetrahydro-1,4-(epiminomethano)naphthalene (11d)

According to General Method A, 7 (0.04 g, 0.1 mmol) was converted to colorless oily 11d (40.1 mg, 70%, 99% purity by ELSD): IR (neat) 2958, 2867, 1500, 1485, 1439, 1361, 1238, 1187, 1038, 928, 908, 771, 732 cm$^{-1}$; $^1$H NMR (400 MHz, CDCl$_3$) δ 7.40 (dd, J=1.2, 8.1 Hz, 1H), 7.03 (dd, J=7.3, 8.0 Hz, 1H), 6.91 (d, J=7.2 Hz, 1H), 6.87 (d, J=1.5 Hz, 1H), 6.79 (dd, J=1.5, 7.9 Hz, 1H), 6.73 (d, J=7.0 Hz, 1H), 5.93 (dd, J=1.4, 5.1 Hz, 2H), 4.80 (s, 2H), 3.78 (AB q, J=13.4 Hz, 2H), 3.57 (t, J=2.5 Hz, 1H), 3.19 (ddd, J=1.7, 4.3, 9.2 Hz, 1H), 2.98 (d, J=1.7 Hz, 1H), 2.07 (dd, J=2.6, 13.5 Hz, 1H), 1.78 (dd, J=4.3, 14.2 Hz, 1H), 1.71 (s, 3H), 1.67-1.61 (m, 1H), 1.33 (s, 3H), 0.93 (dd, J=2.5, 13.6 Hz, 1H), 0.57 (s, 3H); $^{13}$C NMR (100 MHz, CDCl$_3$) δ 147.7, 146.5, 144.4, 142.7, 140.0, 134.1, 129.9, 127.5, 123.1, 121.6, 121.2, 112.8, 109.2, 107.8, 100.9, 56.5, 55.9, 54.8, 49.2, 44.4, 34.6, 32.8, 30.9, 28.2, 22.7; HRMS (ESI) m/z calcd for C$_{25}$H$_{29}$O$_2$BrN (M+H)$^+$ 454.1376, found 454.1370.

General Method B: Reductive Amination.

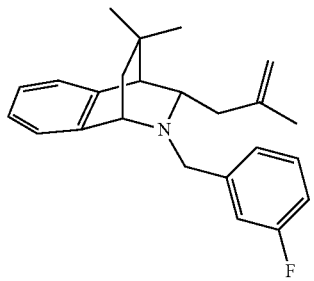 [SMILES: C=C(C)CC1C2c3ccccc3C(CC2(C)C)N1Cc1cccc(F)c1]

(±)-(1S,4R,9S)-10-(3-Fluorobenzyl)-3,3-dimethyl-9-(2-methylallyl)-1,2,3,4-tetrahydro-1,4-(epiminomethano)naphthalene (11a)

To a stirred solution of 8 (16 mg, 0.070 mmol), 3-fluorobenzaldehyde (8.0 mL, 0.077 mmol) and acetic acid (4 mL, 0.07 mmol) in dichloroethane (0.7 mL) was added sodium triacetoxyborohydride (29 mg, 0.14 mmol). The reaction mixture was stirred overnight under argon and then diluted with CH$_2$Cl$_2$ (10 mL). The solution was treated with saturated solution of NaHCO$_3$ (10 mL), and the organic layer was washed with H$_2$O (10 mL) and concentrated under reduced pressure. The crude product was dissolved in THF-H$_2$O (10:1, 1 mL) and treated with NaBH$_4$ (10 mg). The solution was stirred for 3 h at room temperature, quenched with AcOH (1 drop) and diluted with EtOAc (10 mL). The solution was neutralized with a saturated solution of NaHCO$_3$ (5 mL) and washed with H$_2$O (5 mL). The combined organic layers were dried (Na$_2$SO$_4$), and the crude product was purified by chromatography on SiO$_2$ (9:1, hexanes:EtOAc) to give 11a (15 mg, 63%, 99% purity by ELSD) as a colorless oil: IR (neat) 3073, 2927, 1647, 1615, 1590, 1485, 1446, 1359, 1253, 1127, 1069, 928, 890, 783, 754, 714, 684 cm$^{-1}$; $^1$H NMR (400 MHz, CDCl$_3$) δ 7.30-7.20 (m, 3H), 7.19-7.11 (m, 3H), 7.04-7.01 (m, 1H), 6.95 (dt, J=2.6, 8.4 Hz, 1H), 4.78 (s, 1H), 4.66 (s, 1H), 3.92 (AB q, J=13.8 Hz, 2H), 3.60 (t, J=2.5 Hz, 1H), 3.23 (ddd, J=1.7, 4.3, 10.0 Hz, 1H), 2.51 (br s, 1H), 2.13 (dd, J=2.6, 13.3 Hz, 1H), 1.79 (dd, J=4.2, 13.7 Hz, 1H), 1.69 (s, 3H), 1.63-1.57 (m, 2H), 1.34 (s, 3H), 1.01 (dd, J=2.3, 13.3 Hz, 1H), 0.57 (s, 3H); $^{13}$C NMR (100 MHz, CDCl$_3$) δ 164.2, 161.8, 143.5, 143.4, 143.2, 142.0, 139.7, 129.6, 129.5, 127.2, 126.1, 126.0, 124.1, 121.9, 115.5, 115.3, 113.8, 113.6, 112.4, 56.1, 56.0, 55.1, 49.6, 44.3, 35.1, 32.0, 31.9, 28.4, 22.4; HRMS (ESI) m/z calcd for C$_{24}$H$_{29}$FN (M)$^+$ 350.2279, found 350.2266.

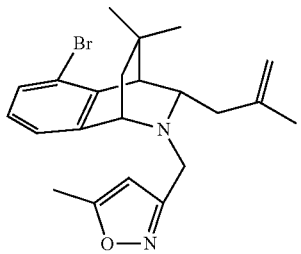 [SMILES: C=C(C)CC1C2c3c(Br)cccc3C(CC2(C)C)N1Cc1cc(C)on1]

(±)-3-(1S,4R,9S)-5-Bromo-3,3-dimethyl-9-(2-methylallyl)-1,2,3,4-tetrahydro-1,4-(epimino-methano)naphthalen-10-yl)methyl)-5-methylisoxazole (11e)

According to General Method B, 7 (25 mg, 0.12 mmol) was converted to pale yellow oily 11e (15 mg, 27%, 98% purity by ELSD): IR (neat) 3073, 2928, 1647, 1606, 1568, 1453, 1358, 1258, 1190, 1139, 1107, 1002, 957, 888, 797, 773, 716, 689 cm$^{-1}$; $^1$H NMR (300 MHz, CDCl$_3$) δ 7.40 (d, J=7.9 Hz, 1H), 7.03 (t, J=7.5 Hz, 1H), 6.94 (d, J=7.0 Hz, 1H), 5.96 (s, 1H), 4.79 (s, 2H), 3.97 (d, J=13.8 Hz, 1H), 3.74 (d, J=13.8 Hz, 1H), 3.58 (t, J=2.4 Hz, 1H), 3.23-3.19 (m, 1H), 2.97 (s, 1H), 2.38 (s, 3H), 2.10 (dd, J=2.6, 13.8 Hz, 1H), 1.77-1.62 (m, 2H), 1.72 (s, 3H), 1.31 (s, 3H), 0.95 (dd, J=2.2, 13.8 Hz, 1H), 0.56 (s, 3H); $^{13}$C NMR (125 MHz, CDCl$_3$) δ 169.5, 163.5, 144.0, 142.6, 139.9, 130.3, 127.7, 123.3, 121.5, 113.2, 101.9, 56.9, 55.9, 49.4, 47.4, 44.7, 34.7, 32.9, 31.0, 28.3, 22.8, 12.5; HRMS (ESI) m/z calcd for C$_{22}$H$_{28}$BrON$_2$ (M+H)$^+$ 415.1380, found. 415.1373.

ELSD): IR (neat) 2928, 2860, 1648, 1568, 1453, 1360, 1275, 1189, 1138, 1102, 1060, 997, 958, 932, 891, 822, 768, 689 cm$^{-1}$; $^1$H NMR (400 MHz, CDCl$_3$) δ 7.37 (dd, J=2.8, 6.3 Hz, 1H), 7.04-6.99 (m, 2H), 4.79 (s, 2H), 3.73 (t, J=2.6 Hz, 1H), 3.03-2.98 (m, 1H), 2.92 (s, 1H), 2.70-2.60 (m, 2H), 2.01 (dd, J=2.6, 13.6 Hz, 1H), 1.86-1.82 (m, 1H), 1.72 (s, 3H), 1.61-1.43 (m, 3H), 1.34-1.22 (m, 7H), 0.93-0.85 (m, 1H), 0.88 (t, J=7.0 Hz, 3H), 0.52 (s, 3H); $^{13}$C NMR (100 MHz, CDCl$_3$) δ 144.3, 142.9, 140.3, 130.3, 127.7, 123.3, 121.7, 112.8, 57.6, 56.4, 53.5, 48.8, 44.7, 34.7, 32.9, 31.1, 30.0, 29.3, 28.2, 23.0, 22.9, 14.3; HRMS (ESI) m/z calcd for C$_{22}$H$_{33}$BrN (M+H)$^+$ 390.1791, found 390.1783.

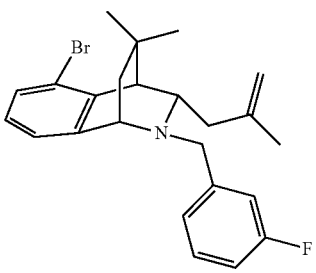 [SMILES: C=C(C)CC1C2c3c(Br)cccc3C(CC2(C)C)N1Cc1cccc(F)c1]

(±)-(1S,4R,9S)-5-Bromo-10-(3-fluorobenzyl)-3,3-dimethyl-9-(2-methylallyl)-1,2,3,4-tetrahydro-1,4-(epiminomethano)naphthalene (11f)

According to General Method B, 7 (25 mg, 0.080 mmol) was converted to colorless oily 11f (13.2 mg, 39%, 98% purity by ELSD): IR (neat) 3074, 2928, 1648, 1614, 1590, 1568, 1485, 1449, 1358, 1253, 1189, 1139, 1123, 1070, 958, 924, 890, 772, 749, 713, 684 cm$^{-1}$; $^1$H NMR (300 MHz, CDCl$_3$) δ 7.44 (dd, J=1.0, 8.0 Hz, 1H), 7.31-7.24 (m, 1H), 7.15-7.04 (m, 3H), 6.99-6.92 (m, 2H), 4.82 (s, 2H), 3.89 (s, 2H), 3.56 (t, J=2.5 Hz, 1H), 3.24 (ddd, J=1.7, 4.4, 8.9 Hz, 1H), 3.02 (d, J=1.6 Hz, 1H), 2.10 (dd, J=2.6, 13.5 Hz, 1H), 1.80 (dd, J=4.4, 14.1 Hz, 1H), 1.74-1.65 (m, 1H), 1.74 (s, 3H), 1.37 (s, 3H), 0.97 (dd, J=2.4, 13.6 Hz, 1H), 0.60 (s, 3H); $^{13}$C NMR (100 MHz, CDCl$_3$) δ 164.3, 161.8, 144.2, 143.0, 142.5, 139.9, 130.0, 129.7, 129.6, 127.5, 124.0, 123.1, 121.2, 115.4, 115.2, 113.9, 113.7, 112.9, 56.6, 55.6, 54.9, 49.2, 44.4, 34.6, 32.8, 30.8, 28.2, 22.7; HRMS (ESI) m/z calcd for C$_{24}$H$_{28}$BrFN (M+H)$^+$ 428.1384, found 428.1371.

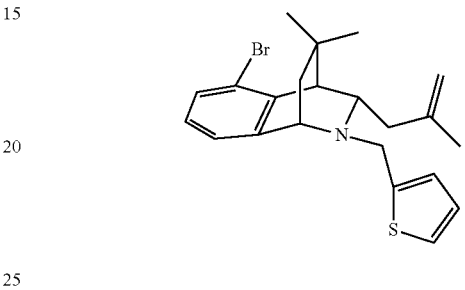

(±)-(1S,4R,9S)-5-Bromo-3,3-dimethyl-9-(2-methylallyl)-10-(thiophen-2-ylmethyl)-1,2,3,4-tetrahydro-1,4-(epiminomethano)naphthalene (11h)

According to General Method B, 7 (0.03 g, 0.09 mmol) was converted to colorless oily 11h (26.3 mg, 67%, 99% purity by ELSD): IR (neat) 3074, 2927, 1647, 1567, 1453, 1360, 1310, 1276, 1189, 1138, 1106, 957, 892, 823, 772, 753, 696 cm$^{-1}$; $^1$H NMR (400 MHz, CDCl$_3$) δ 7.41 (dd, J=1.0, 8.0 Hz, 1H), 7.21 (dd, J=1.5, 4.7 Hz, 1H), 7.04 (dd, J=7.3, 8.0 Hz, 1H), 6.97-6.93 (m, 3H), 4.81 (d, J=5.2 Hz, 2H), 4.15 (d, J=14.0 Hz, 1H), 3.97 (d, J=14.0 Hz, 1H), 3.71 (t, J=2.6 Hz, 1H), 3.22 (ddd, J=1.8, 4.5, 8.7 Hz, 1H), 2.99 (d, J=1.7 Hz, 1H), 2.05 (dd, J=2.6, 13.6 Hz, 1H), 1.81 (dd, J=4.6, 14.0 Hz, 1H), 1.73 (s, 3H), 1.68 (dd, J=8.7, 14.1 Hz, 1H), 1.33 (s, 3H), 0.95 (dd, J=2.5, 13.7 Hz, 1H), 0.58 (s, 3H); $^{13}$C NMR (100 MHz, CDCl$_3$) δ 145.0, 144.3, 142.7, 140.1, 130.2, 127.7, 126.5, 125.0, 123.2, 121.5, 113.1, 56.8, 55.0, 50.9, 49.5, 44.6, 34.8, 32.9, 31.0, 28.4, 23.0; HRMS (ESI) m/z calcd for C$_{22}$H$_{26}$BrNS (M)$^+$ 416.1042, found 416.1036.

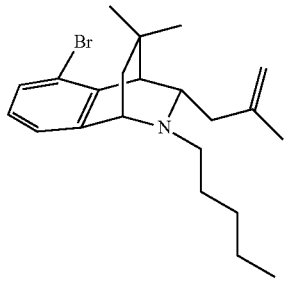 [SMILES: C=C(C)CC1C2c3c(Br)cccc3C(CC2(C)C)N1CCCCC]

(±)-(1S,4R,9S)-5-Bromo-3,3-dimethyl-9-(2-methylallyl)-10-pentyl-1,2,3,4-tetrahydro-1,4-(epiminomethano)naphthalene (11g)

According to General Method B, 7 (0.04 g, 0.1 mmol) was converted to colorless oily 11g (35 mg, 72%, 99% purity by

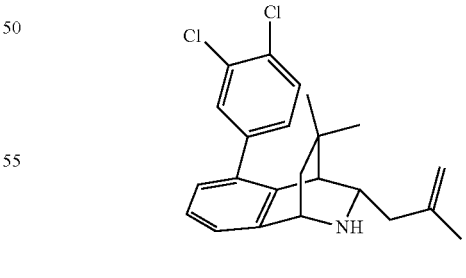

(±)-(1S,4R,9S)-5-(3,4-Dichlorophenyl)-3,3-dimethyl-9-(2-methylallyl)-1,2,3,4-tetrahydro-1,4-(epiminomethano)naphthalene (12a)

A solution of 7 (0.05 g, 0.2 mmol), 3,4-dichlorophenylboronic acid (59.5 mg, 0.310 mmol) and Pd(PPh$_3$)$_2$Cl$_2$ (11 mg, 0.015 mmol) in dioxane (0.7 mL) and 2 M aqueous Na$_2$CO$_3$ (2.2 mL) was heated to 120° C. for 1 h in the microwave. After addition of EtOAc (20 mL) the mixture was washed with H$_2$O (10 mL) and brine (10 mL). The combined organic layers were dried (Na$_2$SO$_4$) and the crude residue was purified by chromatography on Al$_2$O$_3$ (1:1 to 1:2, hexanes:EtOAc) to give 12a (45 mg, 74%, 95% purity by ELSD) as a yellow oil: IR (neat) 2929, 1647, 1548, 1458, 1372, 1274, 1195, 1133, 1078, 1031, 888, 816, 772, 694 cm$^{-1}$; $^1$H NMR (400 MHz, CDCl$_3$) δ 7.72-7.65 (m, 1H), 7.52-7.47 (m, 1H), 7.43 (s, 1H), 7.31-7.26 (m, 1H), 7.19-7.15 (m, 2H), 4.71 (s, 1H), 4.45 (s, 1H), 3.97 (s, 1H), 3.72 (dd, J=4.4, 9.5 Hz, 1H), 2.57 (s, 1H), 1.88 (dd, J=2.8, 12.9 Hz, 1H), 1.80 (dd, J=4.2, 13.6 Hz, 1H), 1.71 (s, 3H), 1.32-1.26 (m, 5H), 0.61 (s, 3H); $^{13}$C NMR (100 MHz, CDCl$_3$) δ 142.5, 142.3, 141.0, 138.5, 136.9, 132.2, 131.5, 131.3, 130.1, 129.1, 127.4, 126.2, 121.8, 112.9, 52.8, 48.5, 47.2, 45.3, 42.6, 32.6, 32.0, 29.0, 22.3; HRMS (ESI) m/z calcd for C$_{23}$H$_{26}$NCl$_2$ (M+H)$^+$ 346.1437, found 346.1428.

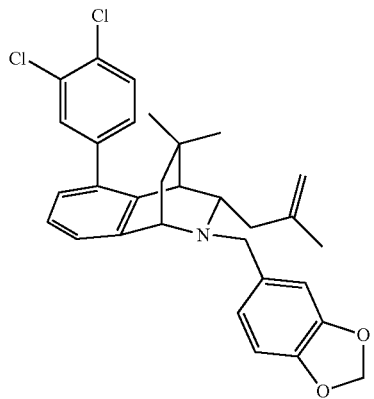 [SMILES: C=C(C)CC1C2c3c(-c4ccc(Cl)c(Cl)c4)cccc3C(CC2(C)C)N1Cc1ccc2c(c1)OCO2]

(±)-(1S,4R,9S)-10-(Benzo[d][1,3]dioxol-5-ylmethyl)-5-(3,4-dichlorophenyl)-3,3-dimethyl-9-(2-methylallyl)-1,2,3,4-tetrahydro-1,4-(epiminomethano)-naphthalene (12b)

A solution of 11d (0.04 g, 0.09 mmol), 3,4-dichlorophenylboronic acid (33.5 mg, 0.170 mmol), Pd(PPh$_3$)$_2$Cl$_2$ (6 mg, 0.009 mmol) and anhydrous sodium carbonate (27 mg, 0.25 mmol) in degassed dioxane (0.5 mL) and H$_2$O (0.15 mL) was heated to 120° C. for 1 h in the microwave and diluted with EtOAc (5 mL). The organic layer was washed with H$_2$O (10 mL), brine (10 mL), dried (Na$_2$SO$_4$), and concentrated. The crude product was purified by chromatography on SiO$_2$ (95:5, hexanes:EtOAc) to give 12b (35.1 mg, 77%, 99% purity by ELSD) as a colorless oil: $^1$H NMR (400 MHz, CDCl$_3$) δ 7.48 (d, J=8.3 Hz, 1H), 7.42 (d, J=2.0 Hz, 1H), 7.25 (t, J=7.3 Hz, 1H), 7.18 (dd, J=2.0, 8.2 Hz, 1H), 7.15 (dd, J=1.3, 7.8 Hz, 1H), 7.04 (dd, J=1.1, 7.2 Hz, 1H), 6.93 (d, J=1.4 Hz, 1H), 6.84-6.77 (m, 2H), 5.98, 5.97 (AB q, J=1.5 Hz, 2H), 4.69 (s, 1H), 4.44 (s, 1H), 3.81, 3.80 (AB q, J=13.4 Hz, 2H), 3.66 (t, J=2.6 Hz, 1H), 3.24 (ddd, J=1.7, 4.5, 8.2 Hz, 1H), 2.71 (d, J=1.4 Hz, 1H), 2.14 (dd, J=2.5, 13.5 Hz, 1H), 1.85 (dd, J=4.4, 15.4 Hz, 1H), 1.71-1.64 (m, 1H), 1.69 (s, 3H), 1.31 (s, 3H), 0.99 (dd, J=2.5, 13.6 Hz, 1H), 0.56 (s, 3H); $^{13}$C NMR (100 MHz, CDCl$_3$) δ 147.8, 146.6, 143.2, 143.0, 141.2, 138.5, 137.7, 134.3, 132.2, 131.5, 131.2, 130.0, 129.2, 127.6, 126.2, 122.4, 121.7, 111.6, 109.3, 108.0, 101.0, 56.3, 56.0, 54.6, 46.7, 44.3, 34.7, 33.2, 32.0, 28.6, 23.5; HRMS (ESI) m/z calcd for C$_{31}$H$_{32}$O$_2$NCl$_2$ (M+H)$^+$ 520.1805, found 520.1788.

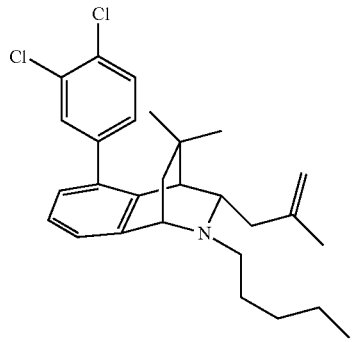 [SMILES: C=C(C)CC1C2c3c(-c4ccc(Cl)c(Cl)c4)cccc3C(CC2(C)C)N1CCCCC]

(±)-(1S,4R,9S)-5-(3,4-Dichlorophenyl)-3,3-dimethyl-9-(2-methylallyl)-10-pentyl-1,2,3,4-tetrahydro-1,4-(epiminomethano)naphthalene (12c)

A solution of 11g (34 mg, 0.090 mmol), 3,4-dichlorophenylboronic acid (33.2 mg, 0.170 mmol), Pd(PPh$_3$)$_2$Cl$_2$ (6 mg, 0.009 mmol), and anhydrous sodium carbonate (26.7 mg, 0.250 mmol) in degassed dioxane (0.5 mL) and H$_2$O (0.15 mL) was heated to 120° C. for 1 h in the microwave and diluted with EtOAc (5 mL). The organic layer was washed with H$_2$O (10 mL), brine (10 mL), dried (Na$_2$SO$_4$), and concentrated. The crude product was purified by chromatography on SiO$_2$ (95:5, hexanes:EtOAc) to give 12c (21.2 mg, 53%, 99% purity by ELSD) as a colorless oil: $^1$H NMR (400 MHz, CDCl$_3$) δ 7.46 (d, J=8.3 Hz, 1H), 7.39 (d, J=2.0 Hz, 1H), 7.29-7.25 (m, 1H), 7.22-7.13 (m, 3H), 4.68 (s, 1H), 4.35 (s, 1H), 3.87 (t, J=2.5 Hz, 1H), 3.09-3.05 (m, 1H), 2.80-2.62 (m, 3H), 2.10 (dd, J=2.6, 13.5 Hz, 1H), 1.90 (d, J=15.0 Hz, 1H), 1.70-1.50 (m, 3H), 1.68 (s, 3H), 1.40-1.25 (m, 4H), 1.26 (s, 3H), 1.01 (dd, J=2.6, 13.5 Hz, 1H), 0.93 (t, J=6.9 Hz, 1H), 0.54 (s, 3H); $^{13}$C NMR (100 MHz, CDCl$_3$) δ 143.2, 142.8, 141.2, 138.6, 137.7, 132.1, 131.5, 131.1, 130.0, 129.2, 127.7, 126.3, 122.7, 111.0, 57.2, 56.1, 53.2, 46.1, 43.9, 34.8, 33.2, 32.1, 30.0, 29.2, 28.3, 23.7, 22.8, 14.3; HRMS (ESI) m/z calcd for C$_{28}$H$_{36}$NCl$_2$ (M+H)$^+$ 456.2219, found 456.2205.

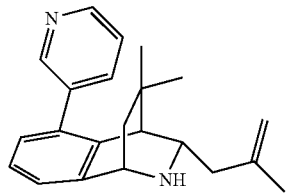 [SMILES: C=C(C)CC1NC2CC(C)(C)C1c1c(-c3cccnc3)cccc12]

(±)-(1S,4R,9S)-3,3-Dimethyl-9-(2-methylallyl)-5-(pyridin-3-yl)-1,2,3,4-tetrahydro-1,4-(epiminomethano)naphthalene (12d)

A solution of 7 (81 mg, 0.25 mmol), pyridine-3-boronic acid (62 mg, 0.50 mmol), and Pd(PPh$_3$)$_2$Cl$_2$ (18 mg, 0.025 mmol) in degassed dioxane (1.1 mL) was treated with a 2 M aqueous solution of Na$_2$CO$_3$ (0.4 mL) and heated to 120° C. for 1 h in a microwave. The reaction mixture was diluted with EtOAc (10 mL) and washed with H$_2$O (10 mL) and brine (10 mL). The combined organic layers were dried (Na$_2$SO$_4$), and the crude residue was purified by chromatography on SiO$_2$ (5:95, MeOH:CH$_2$Cl$_2$ with 0.1% Et$_3$N) to give 12d (19.5 mg, 24%, 97% purity by LC-MS) as a wax: IR (neat) 2928, 1463, 1437, 1405, 1191, 1176, 773, 747, 715 cm$^{-1}$; $^1$H NMR (400 MHz, CDCl$_3$) δ 8.63 (d, J=1.2 Hz, 2H), 7.68-7.65 (m, 1H), 7.37 (dd, J=7.2, 5.5 Hz, 1H), 7.34-7.30 (m, 1H), 7.28 (d, J=1.3 Hz, 1H), 7.22-7.17 (m, 2H), 4.67 (s, 1H), 4.40 (s, 1H), 3.98 (s, 1H), 3.72 (dd, J=9.7, 4.3 Hz, 1H), 2.57 (s, 1H), 1.91-1.86 (m, 1H), 1.79 (dd, J=13.7, 4.2 Hz, 1H), 1.67 (s, 3H), 1.35-1.25 (m, 2H), 1.27 (s, 3H), 0.63 (s, 3H); $^{13}$C NMR (100 MHz, CDCl$_3$) δ 150.3, 148.4, 142.5, 142.3, 137.3, 137.2, 137.0, 136.6, 127.8, 126.3, 123.2, 122.0, 113.0, 52.8, 48.6, 47.2, 45.3, 42.6, 32.6, 32.0, 29.0, 23.0; HRMS (ESI) m/z calcd for C$_{22}$H$_{27}$N$_2$ (M+H)$^+$ 319.2169, found 319.2161.

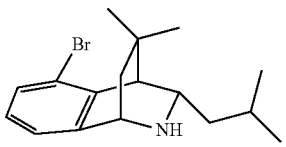 [SMILES: CC(C)CC1NC2CC(C)(C)C1c1c(Br)cccc12]

(±)-(1S,4R,9S)-5-Bromo-3,3-dimethyl-9-(2-methylallyl)-1,2,3,4-tetrahydro-1,4-(epimino-methano)-naphthalene (13)

A solution of 7 (37 mg, 0.11 mmol) in dry EtOAc (0.4 mL) was treated with 5% rhodium on carbon (37 mg) and stirred under a hydrogen atmosphere for 24 h. The catalyst was filtered through Celite and the solvent was removed in vacuo. The crude product was purified by chromatography on SiO$_2$ (100% EtOAc) to give 13 (34 mg, 91%, 99% purity by ELSD) as a yellow oil: IR (neat) 2954, 1564, 1452, 1385, 1366, 1326, 1180, 1116, 1066, 968, 758, 707, 687 cm$^{-1}$; $^1$H NMR (300 MHz, CDCl$_3$) δ 7.43 (dd, J=1.7, 7.3 Hz, 1H), 7.09-7.01 (m, 2H), 3.89 (br t, J=2.9 Hz, 1H), 3.62 (t, J=7.0 Hz, 1H), 2.95 (s, 1H), 1.82 (dd, J=2.7, 13.2 Hz, 1H), 1.77-1.65 (m, 1H), 1.30 (s, 3H), 1.23 (dd, J=3.0, 13.3 Hz, 1H), 0.79 (d, J=6.6 Hz, 3H), 0.78 (d, J=6.6 Hz, 3H), 0.77 (dd, J=6.8, 13.7 Hz, 1H), 0.70-0.50 (m, 1H), 0.58 (s, 3H); $^{13}$C NMR (75 MHz, CDCl$_3$) δ 143.8, 139.3, 130.0, 127.7, 123.6, 121.2, 52.8, 52.7, 49.3, 45.6, 42.1, 32.3, 31.0, 28.7, 24.8, 23.2, 22.7; HRMS (ESI) m/z calcd for C$_{17}$H$_{25}$BrN (M+H)$^+$ 322.1165, found 322.1159.

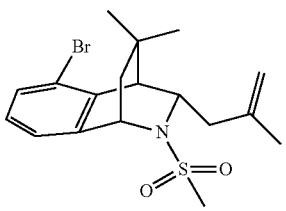 [SMILES: C=C(C)CC1C2c3c(Br)cccc3C(CC2(C)C)N1S(C)(=O)=O]

(±)-(1S,4R,9S)-5-Bromo-3,3-dimethyl-9-(2-methylallyl)-10-(methylsulfonyl)-1,2,3,4-tetrahydro-1,4-(epiminomethano)naphthalene (14a)

A solution of 7 (25 mg, 0.078 mmol) in dry CH$_2$Cl$_2$ (0.8 mL) was treated at 0° C. with triethylamine (22 μL, 0.16 mmol) and methanesulfonyl chloride (7 μL, 0.08 mmol), stirred for 24 h at room temperature, diluted with CH$_2$Cl$_2$ (3 mL), washed with H$_2$O (2×5 mL), dried (Na$_2$SO$_4$), and concentrated. The crude product was purified by chromatography on SiO$_2$ (10-20% EtOAc:hexanes) to give 14a (28.5 mg, 92%, 99% purity by ELSD) as a colorless wax: IR (neat) 3075, 2959, 1650, 1568, 1454, 1319, 1189, 1146, 1121, 1073, 1053, 963, 949, 927, 909, 891, 800, 769, 687, 662 cm$^{-1}$; $^1$H NMR (500 MHz, CDCl$_3$) δ 7.53 (t, J=4.7 Hz, 1H), 7.16 (d, J=4.4 Hz, 1H), 4.89 (s, 1H), 4.79 (s, 1H), 4.74 (s, 1H), 4.53 (d, J=10.4 Hz, 1H), 3.25 (s, 1H), 2.92 (s, 3H), 2.26 (d, J=13.8 Hz, 1H), 2.15 (dd, J=3.1, 13.4 Hz, 1H), 1.79 (s, 3H), 1.51 (dd, J=10.7, 13.7 Hz, 1H), 1.38 (s, 3H), 1.19 (d, J=13.7 Hz, 1H), 0.71 (s, 3H); $^{13}$C NMR (125 MHz, CDCl$_3$) δ 141.0, 140.7, 139.6, 131.6, 128.4, 123.9, 121.8, 114.3, 54.6, 53.2, 49.3, 43.3, 42.7, 42.3, 31.6, 31.1, 28.3, 22.4; HRMS (ESI) m/z calcd for C$_{10}$H$_9$NO$_2$SBr (M−C$_8$H$_{15}$)$^+$ 285.9532, found 285.9526.

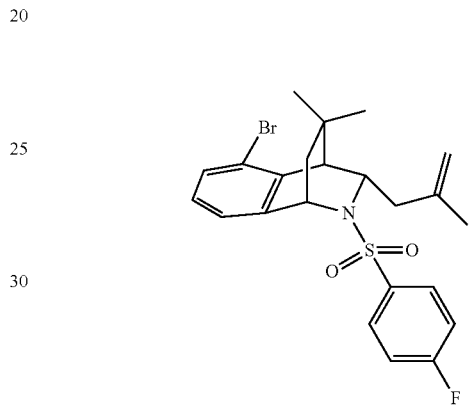

(±)-(1S,4R,9S)-5-Bromo-10-((4-fluorophenyl)sulfonyl)-3,3-dimethyl-9-(2-methylallyl)-1,2,3,4-tetrahydro-1,4-(epiminomethano)naphthalene (14b)

A solution of 7 (25 mg, 0.078 mmol) in dry CH$_2$Cl$_2$ (0.8 mL) was treated at 0° C. with triethylamine (22 μL, 0.16 mmol) and 4-fluorobenzenesulfonyl chloride (16 mg, 0.085 mmol), stirred overnight under argon at room temperature, diluted with CH$_2$Cl$_2$ (5 mL), washed with H$_2$O (10 mL), brine (10 mL), dried (Na$_2$SO$_4$), and concentrated. The crude product was purified by chromatography on SiO$_2$ (4:1, hexanes:EtOAc) to give 14b (25 mg, 67%, 99% purity by ELSD) as a colorless wax: IR (neat) 3075, 2962, 1648, 1592, 1493, 1455, 1349, 1234, 1153, 1090, 946, 908, 839, 769, 732, 682 cm$^{-1}$; $^1$H NMR (500 MHz, CDCl$_3$) δ 7.89-7.85 (m, 2H), 7.51 (dd, J=1.2, 8.0 Hz, 1H), 7.21-7.16 (m, 2H), 7.13 (t, J=7.5 Hz, 1H), 7.09 (d, J=7.3 Hz, 1H), 4.88 (br s, 1H), 4.83 (app t, J=2.5 Hz, 1H), 4.79 (s, 1H), 4.37 (dt, J=2.6, 11.0 Hz, 1H), 3.23 (d, J=2.3 Hz, 1H), 2.33 (d, J=14.2 Hz, 1H), 1.95 (dd, J=3.3, 13.4 Hz, 1H), 1.78 (s, 3H), 1.46 (dd, J=11.1, 14.2 Hz, 1H), 1.11-1.06 (m, 1H), 1.09 (s, 3H); $^{13}$C NMR (125 MHz, CDCl$_3$) δ 166.2, 164.2, 141.2, 140.7, 139.5, 137.8, 131.7, 130.0, 129.9, 128.4, 123.4, 121.9, 116.5, 116.4, 113.9, 54.9, 53.4, 49.2, 42.3, 41.4, 31.6, 31.1, 27.6, 22.6; HRMS (ESI) m/z calcd for C$_{15}$H$_{10}$NO$_2$SFBr (M−C$_8$H$_{15}$)$^+$ 365.9594, found 365.9588.

Example 2

Activity in Heterologous Whole Cell and Cell-Free Preparations

General Biology Methods

Cell Lines:

All cell culture reagents were obtained from Invitrogen, unless indicated. COS-22 (COS-7 cells stably expressing human $p22^{phox}$) and COS-Nox2 (a.k.a. COS-phox) cells (COS-7 cells stably expressing human $p22^{phox}$, Nox2, $p47^{phox}$ and $p67^{phox}$) were kindly provided by Dr. Mary C. Dinauer (Indiana University, School of Medicine) (Price et al., *Blood*, 2002, 99:2653-2661). COS-22 cells were maintained in Dulbecco's Modified Eagle Medium (DMEM) with 4.5 g/L glucose, L-glutamine and sodium pyruvate containing 10% heat-inactivated fetal bovine serum (FBS), 100 units/ml penicillin and 100 µg/ml streptomycin (complete media) supplemented with 1.8 mg/ml G418 (Calbiochem/EMB Bioscience, Gibbstown, N.J.). COS-Nox2 cells were maintained in complete media supplemented with 1.8 mg/mL G418, 1 µg/mL puromycin (Sigma, St Louis, Mo.) and 0.2 mg/mL hygromycin B (Invitrogen, Carlsbad, Calif.). HEK-Nox5 cells were kindly provided by Dr. David Fulton (Georgia Health Sciences University) and maintained in complete media.

Plasmid Preparation, Amplification, and Purification

Plasmids encoding full-length human cDNAs for Nox1 (pcDNA3.1-hNox1), NOXO1 (pcDNA3.1-hNOXO1), NOXA1 (pCMVsport 6-hNOXA1), p47phox (pCMV-Tag4A-hp47) and Nox4 (pcDNA3-hNox4) were kindly provided by Dr. David Lambeth (Emory University, GA). Plasmids encoding Nox1, NOXO1, or NOXA1 were transformed and amplified into *Escherichia coli* strain TOP10 (Invitrogen, Carlsbad, Calif.). Plasmids were purified using a QIAfilter plasmid purification kit (QIAGEN Inc., Valencia, Calif.). For human Nox4 expression, the BglII/NotI restriction fragment from the pcDNA3-hNox4 was subcloned into the plasmid pcDNA3.1/Hygro(−) (Invitrogen, Carlsbad, Calif.) to generate pcDNA3.1/Hygro-hNox4. The fragment sequence, in-frame insertion and orientation were validated by DNA sequencing after PCR amplification. pcDNA3.1/Hygro-hNox4 was amplified into *Escherichia coli* strain TOP10 and purified with a QIAfilter plasmid purification kit.

Transfection:

Cell transfection was carried out using Lipofectamine LTX and Plus reagent (Invitrogen, Carlsbad, Calif., USA), according to the manufacturer's instructions. COS-22 cells were transiently co-transfected with pcDNA 3.1-hNox1, pCMVsport 6-hNOXA1 and pcDNA3.1-hNoxO1 (COS-Nox1/NOXO1/NOXA1 cells) or with pcDNA3.1/Hygro-hNox4 (COS-Nox4 cells). Cells were used 24 hr after transfection. Adherent cells were harvested by incubating with 0.05% trypsin/EDTA for 5 min at 37° C. Following addition of DMEM/10% FBS to neutralize the trypsin, the cells were pelleted by centrifugation at 1100×g for 5 min at 4° C. and used for the experiments.

Measurements of ROS Generation in Whole Cells

L-012 chemiluminescence: COS-Nox2, COS-Nox1/NOXO1/NOXA1, HEK-Nox5 and COS-22 cells were re-plated in OPTIMEM into 384-well white micro-plates (Greiner-Bio One GmbH, Germany) at a density of $2.5 \times 10^3$ cells/well for COS-Nox2 and $5 \times 10^4$ cells/well for all others. The cells were incubated at 37° C. in PBS containing 400 µm L-012 for 10 min. Reaction was initiated by addition of 5 µM PMA in the case of Nox2 or 1 µM PMA/0.1 µM Ionomycin in the case of Nox5. Since Nox1 was constitutively active, Nox1-derived $O_2.^-$ was assessed by comparison to non-transfected cells (Cos22). Luminescence was quantified over time using a Biotek Synergy 4 Hybrid Multi-Mode Microplate Reader. The specificity of L-012 for $O_2.^-$ was confirmed by the addition of SOD (150 U/mL).

Hydrogen Peroxide ($H_2O_2$)-Generating Activity:

$H_2O_2$ production was quantified in intact COS-Nox4 cells by Amplex® Red. Briefly, COS-Nox4 cells ($5 \times 10^4$ cells/ml) were re-plated into 384-well plate in assay buffer (25 mM Hepes, pH 7.4, containing 0.12 M NaCl, 3 mM KCl, 1 mM $MgCl_2$). The cells were incubated in the presence or absence of drugs at 37° C. in assay buffer supplemented with 0.1 mM Amplex® Red, and 0.32 U/ml of horse radish peroxidase (HRP) for 15 min. Fluorescence measurements were made using a Biotek Synergy 4 Hybrid Multi-Mode Microplate Reader with a 530/25-excitation and a 590/35-emission filter. The reaction was monitored at 37° C. for 1 h. A standard curve of known $H_2O_2$ concentrations was included on each plate. Nox4 activity was obtained by calculating the rate of $H_2O_2$ production as RFU/min and then subtracting the equivalent value given by non-transfected COS-22 cells. Similarly, $H_2O_2$ production by Nox2 cells was also measured by Amplex® Red as described above but in the presence of 150 U/mL of SOD and the reaction was initiated by addition of 5 µM PMA. The rate of $H_2O_2$ production in this case was calculated as RFU/min after the subtraction of the equivalent value given by non-stimulated cells. Data are expressed as % of vehicle control.

Measurements of Superoxide Generation in Cell-Free Preparations

Xanthine Oxidase Assay:

Bovine milk XO (grade 1, ammonium sulfate suspension; Sigma-Aldrich) was first desalted using PD-10 columns (Sephadex G-25, GE Healthcare Biosciences, Piscataway, N.J.) equilibrated in PBS. XO activity was assayed by measuring $H_2O_2$ production using the Amplex® Red assay. Reaction mixture contained: 0.02 U/mL XO, 25 mM Hepes, pH 7.4, containing 0.12 M NaCl, 3 mM KCl, 1 mM $MgCl_2$, 0.1 mM Amplex® Red, and 0.32 U/mL of horse radish peroxidase (HRP), reaction was initiated by addition of 1 mM hypoxanthine. Fluorescence was quantified over time using a Biotek Synergy 4 Hybrid Multi-Mode Microplate Reader.

Cytotoxicity Assay:

The cytotoxic effect of compounds was tested using CytoTox-Glo kit (Promega, Madison, Wis.). This assay uses a luminogenic peptide substrate, the AAF-Glo™ Substrate, to measure dead-cell protease activity, which is released from cells that have lost membrane integrity. Cells were plated in 384-well plate at $2.5 \times 10^3$ cells/well in OPTIMEM, incubated for 15 min with the compounds at various concentrations and then carried out dead cell measurements according to manufacturer protocol. Fluorescence signals before and after the addition of digitonin were used to calculate the % of dead cells in each independent well.

Cytochrome C Assay:

COS-Nox2, COS-Nox1/NOXO1/NOXA1 and COS-22 cells were suspended to a concentration of $5 \times 10^7$ cells/ml in ice-cold disruption buffer (8 mM potassium, sodium phosphate buffer pH 7.0, 131 mM NaCl, 340 mM sucrose, 2 mM $NaN_3$, 5 mM $MgCl_2$, 1 mM EGTA, 1 mM EDTA and protease inhibitor cocktail) (Price et al., *Blood,* 2002, 99:2653-2661; Molshanski-Mor et al., *Methods Mol. Biol.,* 2007, 412:385-428). The cells were lysed by freeze/thaw cycles (5 cycles), and passed through a 30-gauge needle 5 times to further lyse the cells. Cell disruption was confirmed by phase contrast microscopy. The cell lysate was centrifuged at 1000×g for 10 min at 4° C. to remove unbroken cells, nuclei and debris. Throughout all procedures, extreme care was taken to maintain the lysate at a temperature close to 0° C. Superoxide ($O_2.^-$) production was calculated from the initial linear rate (over 10 min) of SOD-inhibitable cytochrome c reduction quantified at 550 nm using the extinction coefficient of 21.1 $mM^{-1}$ $cm^{-1}$ (Biotek Synergy 4 Hybrid Multi-Mode Microplate Reader). The oxidase assay buffer consisted of 65 mM sodium phosphate buffer (pH 7.0), 1 mM EGTA, 10 μM FAD, 1 mM $MgCl_2$, 2 mM $NaN_3$ and 0.2 mM cytochrome C. The components of the cell-free system were added in the following order: oxidase assay buffer, cell lysate (5×10⁵ cell equivalents/well) and drugs at a final concentration as shown on individual graphs. The plates were placed on an orbital shaker to mix contents for 5 min at 120 movements/min at room temperature. LiDS, an established lipid activator of phagocyte cell-free system, was added at a concentration of 130 μM and $O_2.^-$ production was initiated by the addition of 180 μM NADPH.

Statistical Analysis:

All data are expressed as means±SEM. $IC_{50}$ values were determined using the GraphPad Prism software (GraphPad Software, San Diego, Calif.) for non-linear regression three-parameters, with constrain values of 100 and 0 for top and bottom, respectively, and assumes a Hill slope of 1.

Results and Discussion

Heterologous Nox1, 2, 4, and 5 cell systems were used as a testing paradigm to identify a probe molecule that inhibits Nox2 selectively over Nox1, 4, and 5. An acceptable probe would also show a lack of activity against XO, which also produces ROS. The latter screen would serve two purposes: (1) to eliminate drugs that inhibit an oxidase of distinct composition; and (2) to preclude agents that directly scavenge ROS. A cell-based primary assay using stable Nox2-transfected COS cells (Price et al., *Blood* 2002, 99:2653-2661) with L-012 chemiluminescence (Daiber et al., *Free Radic. Biol. Med.* 2004, 36:101-111) was used as a detection system for $O_2.^-$ generation.

Screening a subset of small organic molecules from the University of Pittsburgh Chemical Methodologies and Library Development (UPCMLD) library at concentrations of 100, 50, 25, and 12.5 μM led to the identification of hit compound 7. Structurally related compounds 8 and 9 were also present in the screening library, which allowed for some initial structure activity relationship (SAR) information to be gained. Compound 8 was inactive, suggesting that substitution at the 5-position of the heterocycle was important for activity. In contrast, compound 9 was active, suggesting that substitution could also be tolerated at C-8 of the bridged tetrahydroisoquinoline motif.

7

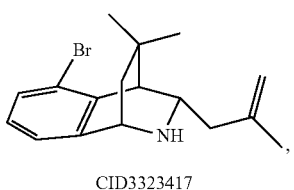

CID3323417

8

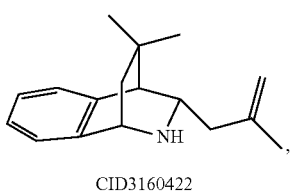

CID3160422

9

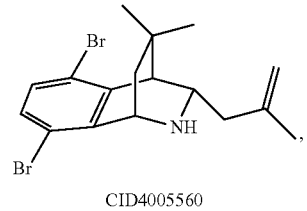

CID4005560

A series of secondary assays was used to confirm activity and rule out undesirable mechanisms of action. First, the concentration-dependent effect of compound 7 was studied using the same conditions as the primary screen (L-012 chemiluminescence in COS-Nox2 cells) revealing that compound 7 had an $IC_{50}$ of 45 μM (FIG. 1, closed squares). Effect of compound 7 on Nox2 activity was measured in whole COS-Nox2 cells stimulated by 5 μM PMA (phorbol 12-myristate 13-acetate) using L-012 and Amplex® Red (AR). Data are expressed as % of vehicle control and represent the mean±SEM of 6 independent experiments.

Figure 2:
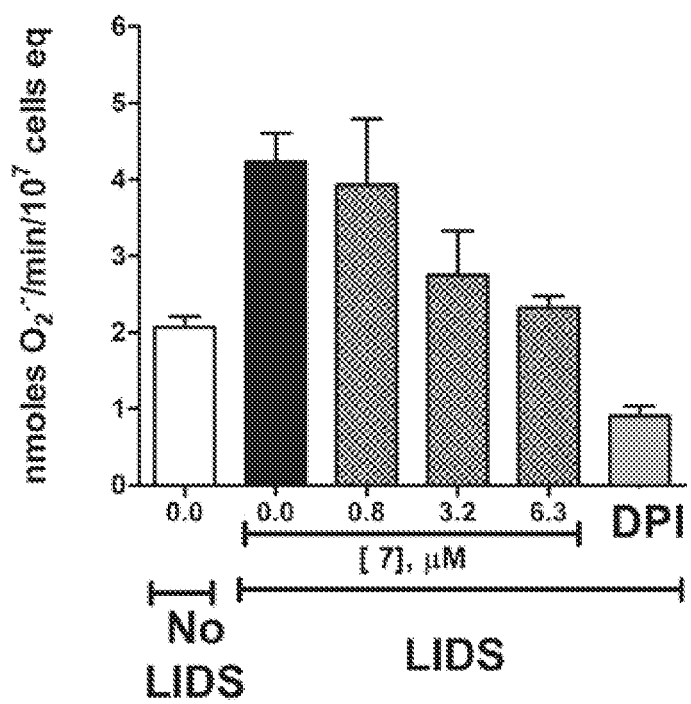
FIG. 2 is a graph showing concentration response testing of compound 7 in lysed COS-Nox2 cells (cell-free preparation).

Cell-free activity in lysed COS-Nox2 cells was promising, since compound 7 was also able to inhibit $O_2.^-$ production in a system in which assembly of active Nox2 subunits is achieved by treatment with the anionic amphiphile LiDS (lithium dodecyl sulfate) and the reaction is initiated by cofactor NADPH (Molshanski-Mor et al., *Methods Mol. Biol.* 2007, 412:385-428). COS-Nox2 cell lysate was preincubated with various concentrations of compound 7 for 15 min at 25° C. After the addition of 130 μM LiDS, $O_2.^-$ production was initiated by the addition of 180 μM NADPH and measured by the initial linear rate of SOD-inhibitable cytochrome C reduction. $O_2.^-$ production is expressed as nmol $O_2.^-$/min/10⁷ cell equivalents. Under these conditions, compound 7 appeared to be effective at inhibiting Nox2 activity since 6.3 μM ameliorated LiDS-stimulated $O_2.^-$ generation to almost non-stimulated levels (FIG. 2).

Figure 3:
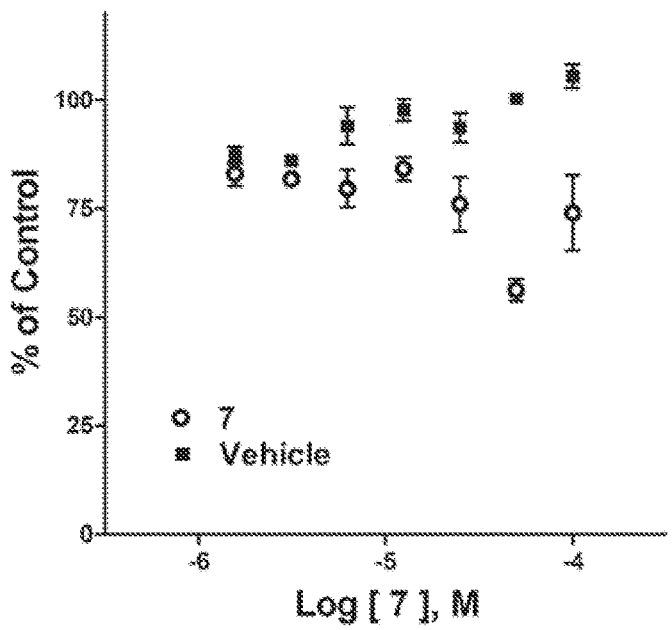
FIG. 3 is a graph showing concentration response testing of compound 7 in COS-Nox4 cells.

Next, because selectivity over the closely related isoform Nox4 was one of our most stringent benchmarks, the concentration-response activity of compound 7 against this isoform was tested. Since Nox4 is generally accepted to directly form $H_2O_2$ rather than $O_2.^-$, the more appropriate Amplex® Red (Life Technologies) fluorescence was used as the detection reporter in Nox4 transfected COS cells (Nisimoto et al., *Biochemistry* 2010, 49:2433-2442); and it was compared to similar assay conditions using the COS-Nox2 cells with addition of SOD to convert $O_2.^-$ to $H_2O_2$. COS-Nox4 cells were pretreated with various concentrations of compound 7 for 15 min. Initial rate of $H_2O_2$ production was measured using Amplex® Red. Data are expressed as the mean±SEM of 7 independent experiments. Compound 7 had an $IC_{50}$ of 40 μM against Nox2-expressing cells when ROS inhibition was assessed using Amplex® Red (FIG. 1, open circles), thus validating our results using two distinct ROS-detection assays. However, compound 7 was found to be inactive against Nox4 (FIG. 3). Finally, the structure of compound 7 was confirmed by resynthesis, and the freshly prepared sample retained its biological activity.

Figure 4:
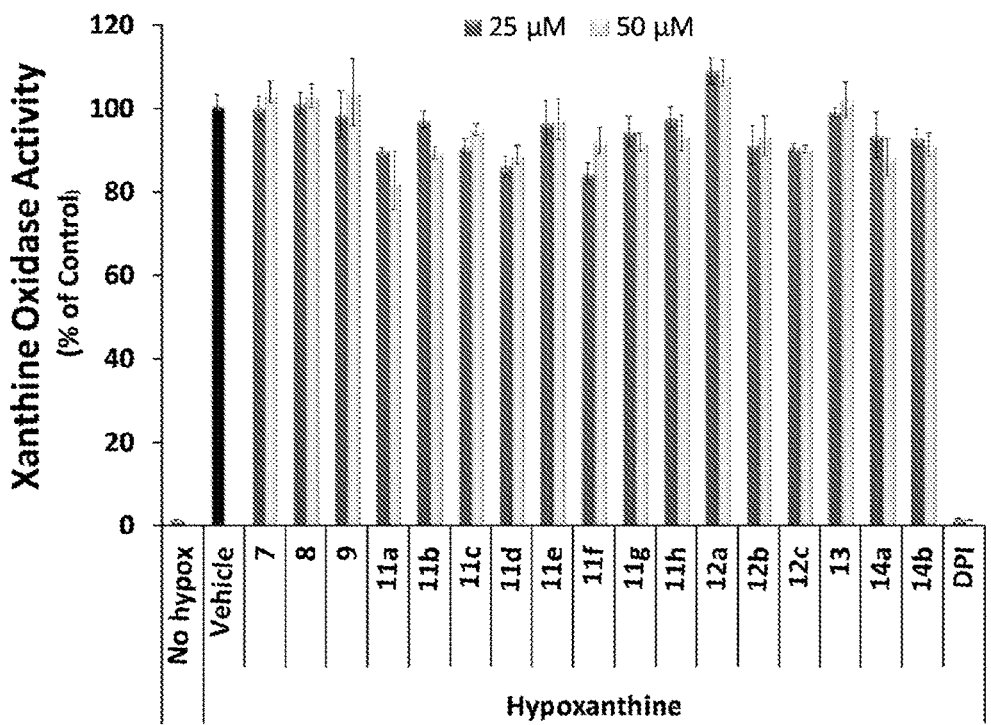
FIG. 4 is a graph showing xanthine oxidase activity of compound 7 and its analogs; each compound was tested at concentrations of 25 µM and 50 µM.

An acceptable selective Nox2 probe would not only be inactive against other Nox isoforms but should also lack non-specific effects such as inhibition of another major source of $O_2.^-$ in mammalian cells or ability to scavenge $O_2.^-$. To determine that the observed Nox inhibition of the tetrahydroisoquinolines was not due to non-specific activities, ROS production by XO was measured in the presence of various concentrations of the analogs. None of the compounds tested showed any significant effect on ROS levels as detected by Amplex® Red, and the activity was compared to complete inhibition by DPI. The results are shown in FIG. 4. Data are expressed as % of vehicle control. These data corroborate that these compounds neither inhibit XO, scavenge ROS, nor interfere with the assay signals.

Figure 5:
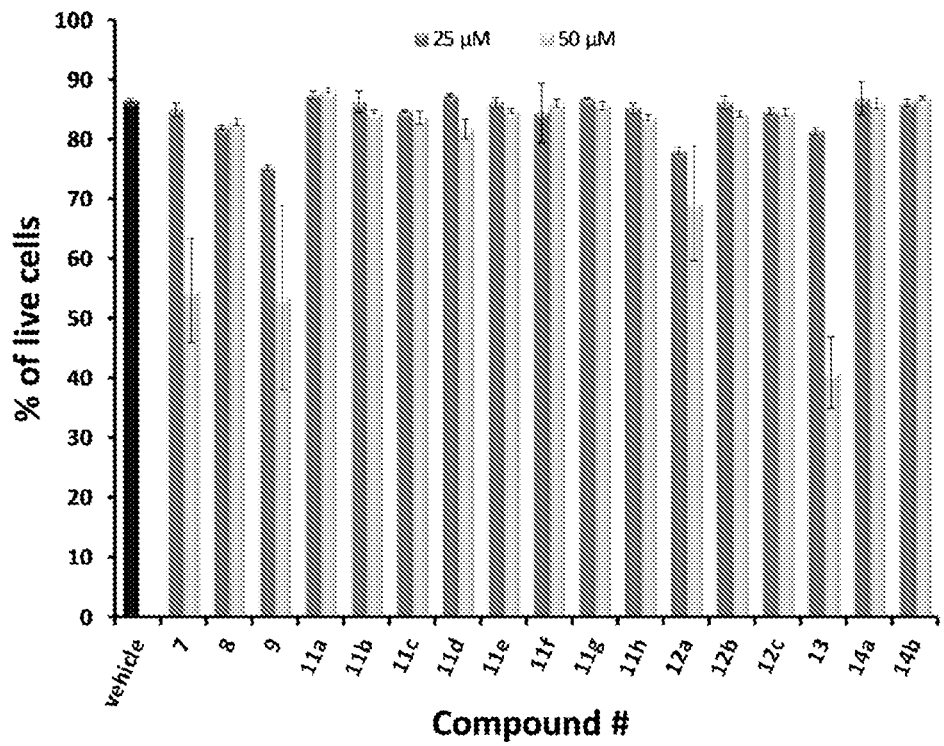
FIG. 5 is a graph showing cytotoxicity data for compound 7 and its analogs; each compound was tested at concentrations of 25 µM and 50 µM.

Another undesirable side effect would be the reduction of ROS production in the assays due to cell death rather than an inhibition of Nox2. To verify that this was not the case for these tetrahydroisoquinolines, the effect of various concentrations of the compounds on cell viability was determined using a commercially available CytoTox-Glo assay (Promega). This assay measures the concentration of proteases released from cells that have lost membrane integrity (i.e., dead cells). The results are shown in FIG. 5. Data are expressed as % of live cells in each independent well (=100−% dead cells). Only compounds 7, 9, and 13, and only at the highest concentration tested, had any effect on cell viability With the confirmation that the analogs were not XO inhibitors, ROS scavengers, or cytotoxic, the selectivity of their inhibition for the Nox isoforms was evaluated. The specificity of compound 7 and analogs against Nox2 activity was determined by a concentration-response analysis of the effect of the tetrahydroisoquinoline derivatives on Nox2-, Nox1-, Nox4-, and Nox5-dependent ROS generation. These data are summarized in Table 2.

matic heterocyclic side chains decreased (11d) or completely abolished (11b, 11c) Nox2 inhibitory activity. In contrast, analogs with relatively smaller N-substituents (11a, 11e-11h) were active against Nox2; but many also inhibited Nox5 activity (11a, 11e, 11f). The 5-substituted 3,4-dichloroaryl analog 12a, exhibited comparable Nox2 and Nox5 activity as the hit compound 7 but displayed greater selectivity over Nox1. On the other hand, when this 3,4-dichloro substitution was combined with the tertiary amine groups n-pentyl and benzodioxole from the analogs 11d and 11g, the hybrid compounds 12b and 12c were inactive. Further attempts to improve the potency and selectivity of compound 12a by forming the C5-substituted pyridyl analog 12d were unsuccessful as this compound was inactive against Nox2 and was therefore not screened against other Nox isoforms. Additionally, aryl and alkyl sulfonamides in place of the tertiary amine completely abolished activity (14a, 14b).

Figure 6:
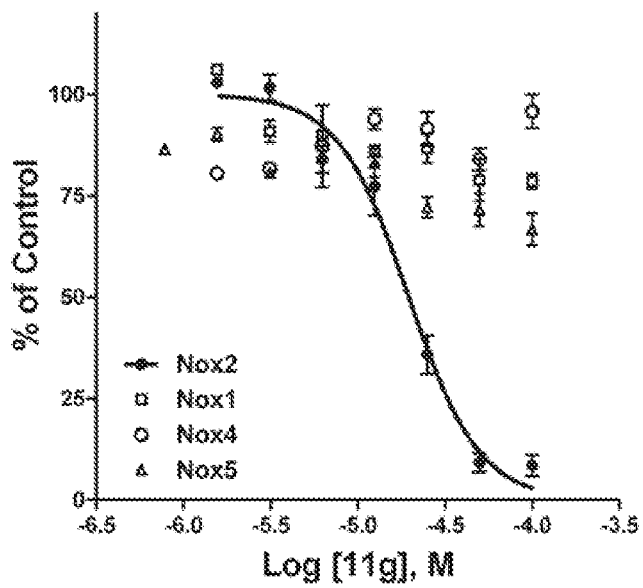
FIG. 6 is a graph showing the concentration response analysis of one embodiment of a Nox2 inhibitor, compound 11g, for inhibition of Nox1, 2, 3, 4, and 5. $IC_{50}$ values were calculated using the non-linear regression for three parameters analysis, which assumes a Hill slope=1.
Figure 7:
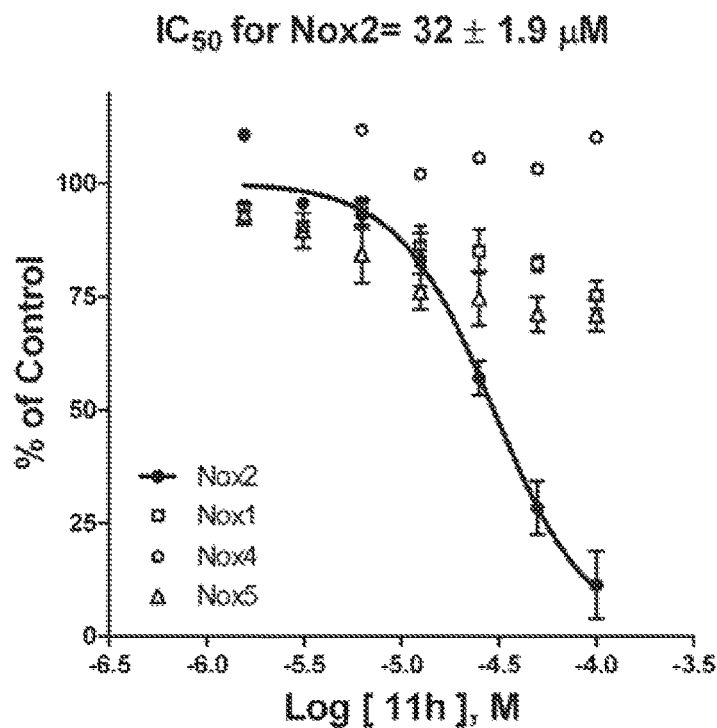
FIG. 7 is a graph showing the concentration response analysis of one embodiment of a Nox2 inhibitor, compound 11h, for inhibition of Nox1, 2, 3, 4, and 5. $IC_{50}$ values were calculated using the non-linear regression for three parameters analysis, which assumes a Hill slope=1.

Compounds 11g and 11h were the most potent and selective among the tetrahydroisoquinoline analogs (IC$_{50}$: 20±1.9 µM and 32±1.9 µM respectively). Both of these agents showed specificity for Nox2 over Nox1, 4, and 5, as demonstrated by cell-based assays for each independent Nox system (Table 2, FIG. 6 (compound 11g), FIG. 7 (compound 11h)). Without wishing to be bound by any particular theory of operation, the SAR emerging from lead compound 7 suggests that small substituents such as n-pentane (11g) and thiophene (11h) on the nitrogen atom influence the selectivity of this scaffold toward Nox2 inhibition.

TABLE 2

IC$_{50}$ values of inhibitors of ROS generation in Nox enzymes.

| Compound | Nox2$^a$ (µM) | Nox2$^b$ (µM) | Nox1$^b$ (µM) | Nox4$^a$ (µM) | Nox5$^b$ (µM) |
| --- | --- | --- | --- | --- | --- |
| 7, CID3323417 | 40 ± 9.7 | 46 ± 11 | 31 ± 0.7 | >100 | 20 ± 3.1 |
| 9, CID4005560 | 25 ± 10 | 40 ± 2.8 | 60 ± 36 | NI | 36 |
| 8, CID3160422 | >100 | >100 | >100 | NI | >100 |
| 13 | 78 ± 19 | 31 ± 3.8 | 32 ± 18 | >100 | 18 ± 1 |
| 11a | 30 ± 7.5 | 68 ± 33 | >100 | >100 | 50 ± 9.0 |
| 11b | >100 | >100 | >100 | NI | >100 |
| 11c | >100 | >100 | >100 | NI | >100 |
| 11d | 40 | 88 ± 22 | >100 | >100 | >100 |
| 11e | 12 ± 0.5 | 48 ± 23 | >100 | >100 | 31 ± 11 |
| 11f | 51 | 68 ± 22 | >100 | >100 | 79 ± 30 |
| 11g | 20 ± 1.9 | 20 ± 4.9 | >100 | >100 | >100 |
| 11h | 32 ± 1.9 | 38 ± 11 | >100 | NI | >100 |
| 12a | 64 ± 35 | 9.0 ± 0.9 | >100 | >100 | 14 ± 0.6 |
| 12d | NI | NI | ND | ND | ND |
| 12b | >100 | >100 | >100 | NI | >100 |
| 12c | 79 | >100 | >100 | >100 | >100 |
| 14a | 27 ± 4.7 | >100 | NI | >100 | >100 |
| 14b | >100 | >100 | >100 | NI | >100 |

$^a$Amplex ® Red assay;
$^b$L-012 assay;
ND = not determined;
NI = not inhibitory (no inhibition seen in the slope of the curves);
>100: indicates a notable slope decrease that allowed for extrapolation of an IC$_{50}$ > 100 µM.
Nox2 activity was measured in whole COS-Nox2 cells stimulated with 5 µM PMA. Constitutive Nox1 activity was measured in transiently transfected Cos-Nox1 cells. Nox5 activity was measured from HEK-Nox5 cells stimulated with 1 µM PMA and 0.5 µM ionomycin. Constitutive Nox4 activity was measured using transiently transfected COS-Nox4 cells. Data are expressed as % of vehicle control and represent the mean ± SEM of 3-7 independent experiments.

Compounds 7 and 9 inhibited Nox2 with IC$_{50}$ values in the range of 25-40 µM but were also found to be active against both Nox1 and 5. Compound 8 from the original screen remained inactive against all Nox isoforms. The alkene moiety was found not to be an essential structural element for activity as the saturated derivative 13 retained inhibitory activity of Nox2, 1, and 5 at concentrations comparable to parent compound 7. Based on the assay results with reductive amination products 11a-h, bulky aro- Compounds 11g and 11h displayed considerably lower IC$_{50}$ values (~30 nM) when tested in a cell-free system (data not shown). These compounds are likely more potent due to enhanced access to the enzyme in the disrupted cell membrane environment.

Compounds 11g and 11h are highly efficacious inhibitors of Nox2 and display virtually no effect on Nox1, 4, or 5, nor xanthine oxidase activity. Furthermore, their inhibitory effects are not due to a nonspecific or undesirable mechanism, such as xanthine oxidase inhibition, ROS scavenging, or cytotoxicity. The small molecule inhibitors 11g and 11h will prove useful as probes to more fully discern the biological role of Nox2 as compared to other Nox isoforms and could potentially serve as a platform for developing therapeutic agents for the treatment of Nox2-related diseases.

Example 3

Activity in Human and Rodent Cell Systems

Methods

Cell Lines:

Cos-Nox2, Cos-Nox1, human fibroblasts were cultured in DMEM, 10% FBS-supplemented media, human pulmonary artery endothelial cells were cultured in EBM2 media containing growth factors (Lonza) and rat neonatal cardiomyocytes were cultured in DMEM/F12 (50/50) media supplemented with 5% horse serum, 100 µM BrdU and Insulin-Transferrin-Selenium (ITS, Gibco).

Transfection:

Cell transfection was carried out using Lipofectamine LTX and Plus reagent (Invitrogen, Carlsbad, Calif., USA), according to the manufacturer's instructions. COS-22 cells were transiently co-transfected with pcDNA 3.1-hNox1, pCMVsport 6-hNOXA1 and pcDNA3.1-hNoxO1 (COS-Nox1/NOXO1/NOXA1 cells) or with pcDNA3.1/Hygro-hNox4 (COS-Nox4 cells). Cells were used 24 hr after transfection. Adherent cells were harvested by incubating with 0.05% trypsin/EDTA for 5 min at 37° C. Following addition of DMEM/10% FBS to neutralize the trypsin, the cells were pelleted by centrifugation at 1100×g for 5 min at 4° C. and used for the experiments.

Cell Homogenates:

Cells were suspended to a concentration of $5 \times 10^7$ cells/ml in ice-cold disruption buffer (8 mM potassium, sodium phosphate buffer pH 7.0, 131 mM NaCl, 340 mM sucrose, 2 mM $NaN_3$, 5 mM $MgCl_2$, 1 mM EGTA, 1 mM EDTA and protease inhibitor cocktail). The cells were lysed by freeze/thaw cycles (5 cycles), and passed through a 30-gauge needle five times to further lyse the cells. Cell disruption was confirmed by phase contrast microscopy. The cell lysate was centrifuged at 1000×g for 10 min at 4° C. to remove unbroken cells, nuclei and debris. Throughout all procedures, extreme care was taken to maintain the lysate at a temperature close to 0° C.

Cytochrome C Assay:

Superoxide ($O_2.^-$) production from cell homogenates was calculated from the initial linear rate (over 10 min) of SOD-inhibitable cytochrome c reduction quantified at 550 nm using the extinction coefficient of 21.1 mM-1 cm-1 (Biotek Synergy 4 Hybrid Multi-Mode Microplate Reader). The oxidase assay buffer consisted of 65 mM sodium phosphate buffer (pH 7.0), 1 mM EGTA, 10 µM FAD, 1 mM MgCl2, 2 mM NaN3 and 0.2 mM cytochrome C.

Hypertrophy Measurements:

Hypertrophy was assessed by measurement of cardiomyocytes length using ImageJ public domain software (developed by the National Institutes of Health).

Immunoprecipitation:

300 µg of cell homogenates were diluted in 0.3 ml HBSS buffer and incubated with 1.25 µg of α-p47$^{phox}$ antibody (Santa Cruz Biotechnology). After overnight incubation at 4° C. with constant agitation, 10 µl of Protein G-Agarose slurry were added to each sample to pull-down p47$^{phox}$: antibody complex. Beads were washed, boiled, run on PAGE-SDS gels and then blotted on nitrocellulose membrane. Western blot analysis was carried out using antibodies against p47$^{phox}$ and Nox2. Bands were visualized using Odyssey software from Licor and then quantified using ImageJ software.

Results and Discussion $IC_{50}$ of Compound 11g is Lower in Cell Homogenates than in Whole Cells.

Figure 8:
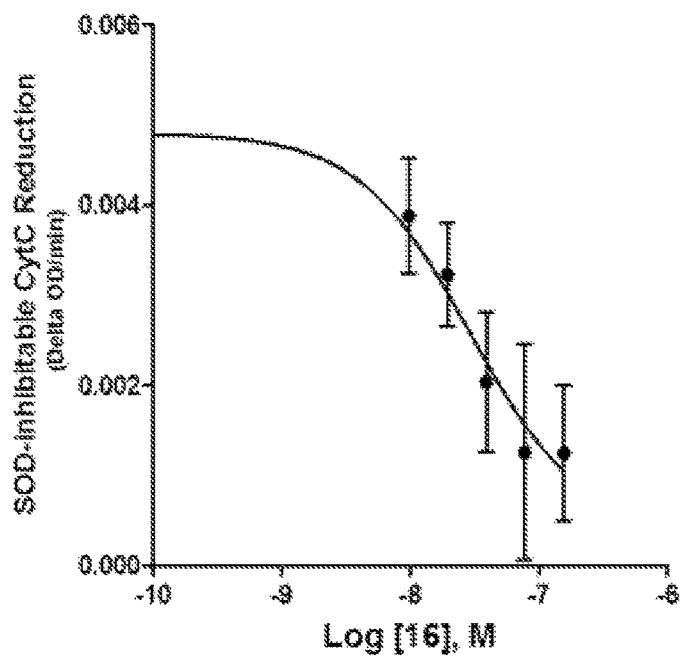
FIG. 8 is a graph showing the concentration response analysis of one embodiment of a Nox2 inhibitor, compound 11g, for inhibition of Nox2 activity in cell homogenates.

The $IC_{50}$ of the compound 11g in ROS production by Nox2 cell homogenate stimulated with LiDS was assessed and determined to be 32.4±9.0 nM, 100-fold lower in magnitude than that for whole cells (FIG. 8). This study not only demonstrated the high efficiency of this compound in cell homogenates where the issue of cell internalization is avoided, but also indicated a direct action on the enzyme since under these conditions the enzyme stimulation by LiDs bypasses activation of protein kinase C.

Effect of Compounds 11g and 11h on Superoxide Production by a Variety of Cell Systems.

Figure 9:
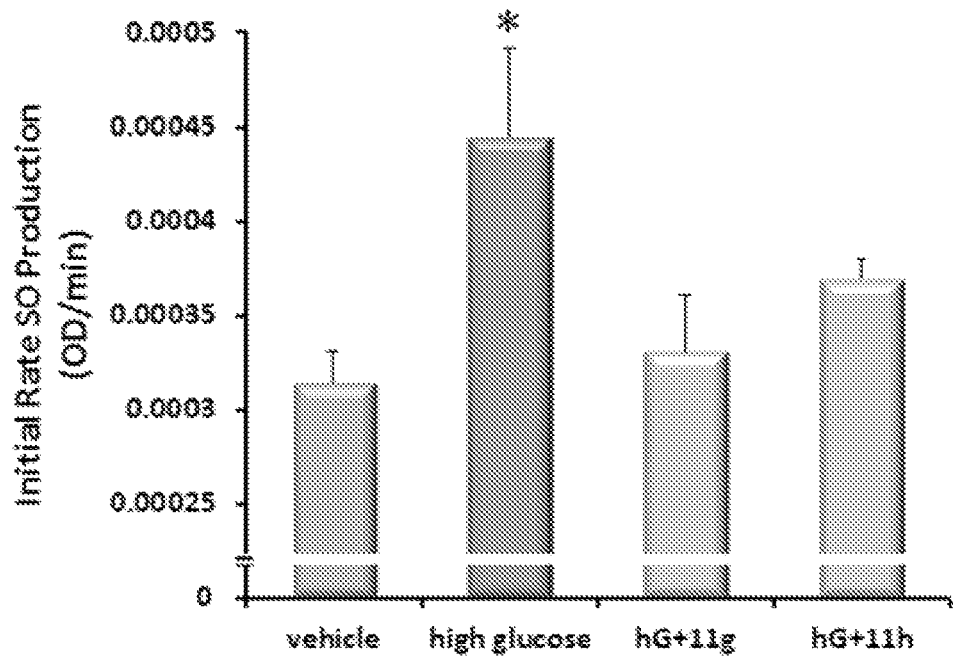
FIG. 9 is a graph showing the effects of 25 µM compound 11g and compound 11h on reactive oxygen species (ROS) production of human pulmonary artery endothelial cells (HPAEC) treated with high glucose (25 mM) for 24 hours.

Compounds 11g and 11h subsequently were tested in parenchymal cell lines where more than one Nox could be present and activated. Human pulmonary artery endothelial cells (HPAEC) were treated with high glucose (25 mM) for 24 hr in the presence or absence of the compounds. High glucose treatment, as in diabetes, has been suggested to stimulate ROS production by stimulation of Nox2 activity. Under these conditions both compounds 11g and 11h attenuated the high glucose-stimulated superoxide production (FIG. 9).

Figure 10:
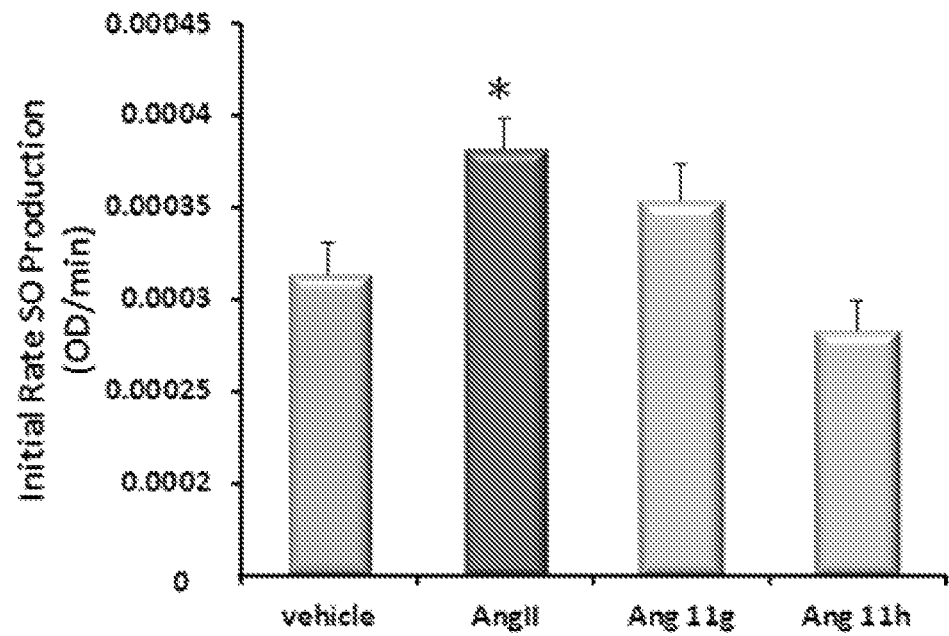
FIG. 10 is a graph showing the effects of 25 µM compound 11g and compound 11h on ROS production of HPAEC treated with angiotensin II (AngII) for 24 hours.

Preliminary data showed that ROS production by these same cells could also be stimulated by treatment with angiotensin II (AngII) for 24 hrs. However compounds 11g and 11h had a differential effect on this response as compared to that to glucose stimulation (FIG. 10). This suggests a unique mechanism of action for each compound.

Figure 11:
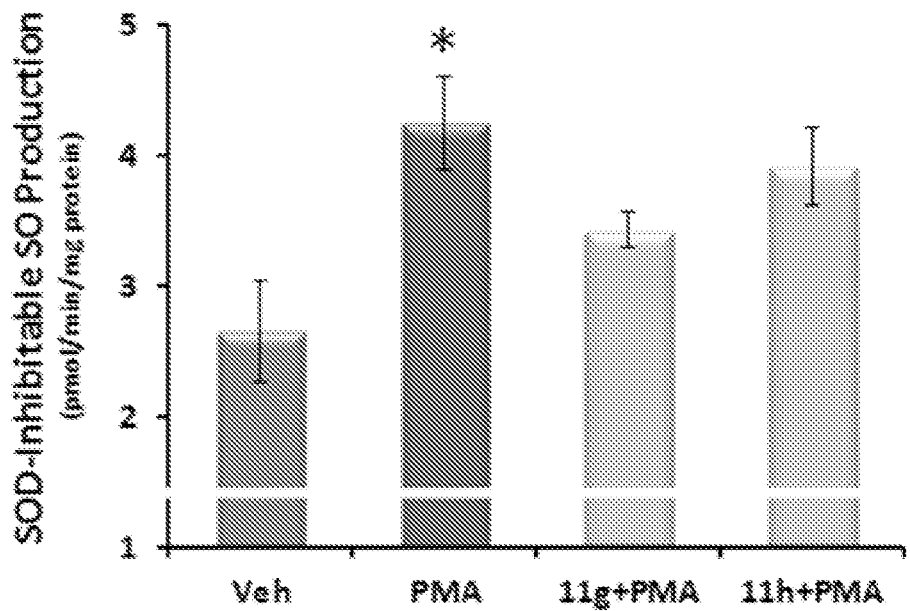
FIG. 11 is a graph showing the effects of 10 µM compound 11g and compound 11h on ROS production of human fibroblasts treated with phorbol ester (PMA).

Compounds 11g and 11h also were evaluated for potential inhibitory activity in phorbol ester (PMA)-stimulated ROS production by human fibroblasts. As expected PMA, an activator of protein kinase C, stimulated superoxide production. This effect was attenuated by both compounds at a concentration of 10 µM (FIG. 11).

Compounds 11g and 11h could Interfere with p47$^{phox}$ Binding to p22$^{phox}$ Through Interaction with p47$^{phox}$-SH3 Domains.

Figure 12:
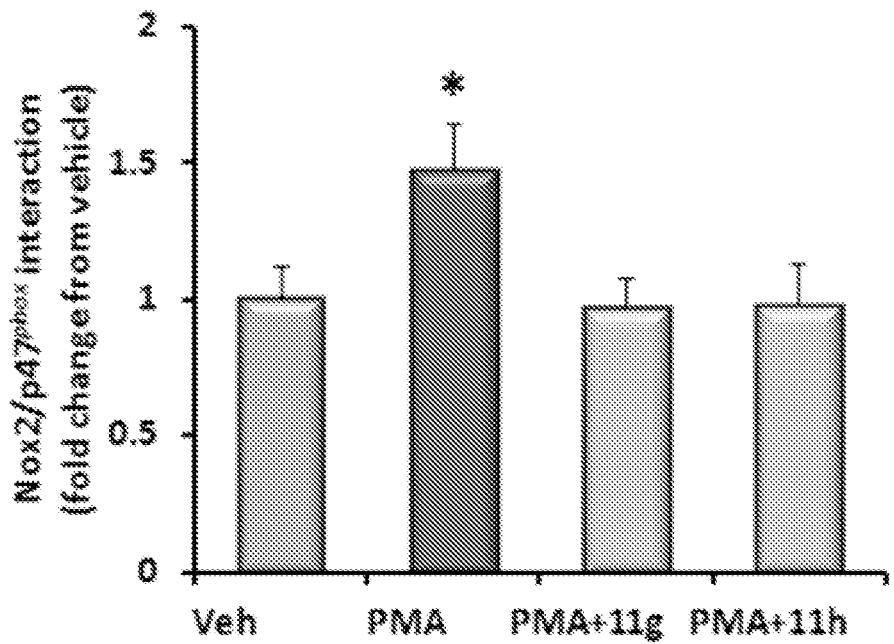
FIG. 12 is a graph showing the change in co-immunoprecipitation of Nox2/p47$^{phox}$ in Cos-Nox2 cells preincubated with compound 11g and 11h using an antibody against p47$^{phox}$.

To interrogate a mode of Nox2 inhibition, in silico interaction analysis of pre-existing atomic structures was employed. These docking analyses suggested binding of compounds 11g and 11h to the p47$^{phox}$-SH3 binding surface which is responsible for its interaction with p22$^{phox}$. To further investigate this type of interaction and inhibition, co-immunoprecipitation was used and p47$^{phox}$ association with cytochrome b558 in Cos-Nox2 cells. While PMA promoted a significant association between the p47$^{phox}$ and Nox2 (the major cytochrome b558 subunit), pre-incubation with both 11g and 11h significantly attenuated the interaction by 34.3±6.07 and 33.45±6.08% respectively (FIG. 12). Furthermore, translocation of p47$^{phox}$ to the plasma membrane was assessed by isolation of 100,000×g fractions and showed a significant reduction in p47$^{phox}$ expression (data not shown).

Figure 13:
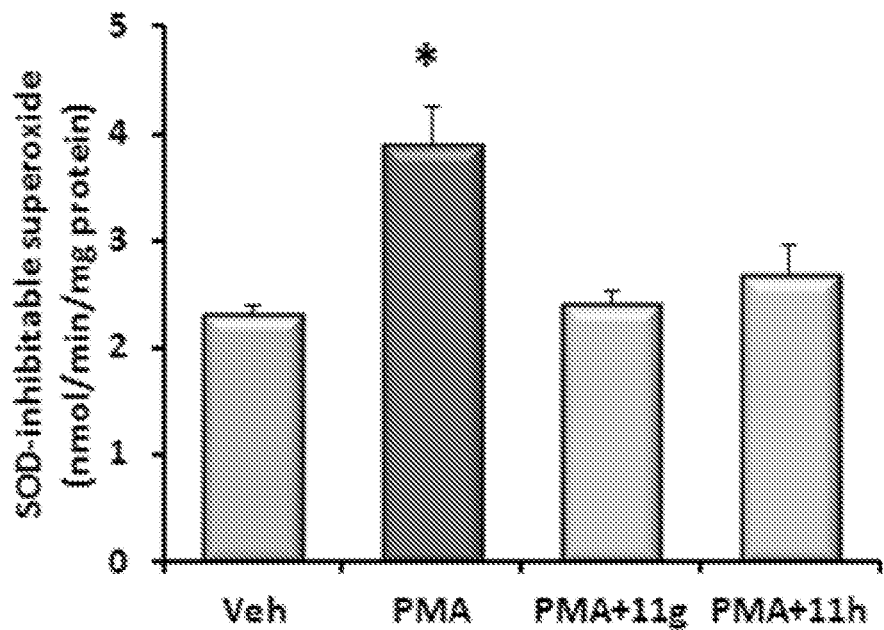
FIG. 13 is a graph showing the effects of 10 µM compound 11g and compound 11h on transiently Nox2-transfected Cos cells treated with PMA.
Figure 14:
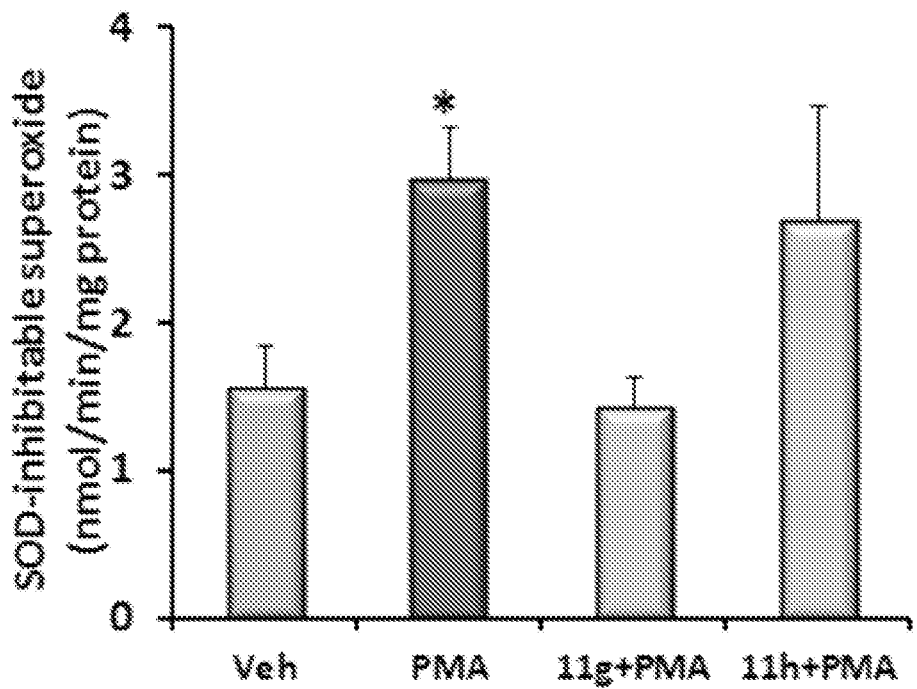
FIG. 14 is a graph showing the effects of 10 µM compound 11g and compound 11h on transiently Nox1 hybrid system-transfected Cos cells treated with PMA.

Since p47$^{phox}$ activation is important not only for Nox2 activity but also for Nox1 hybrid system present mainly in human endothelial cells, the effect of compounds 11g and 11h on ROS production of transiently Nox2-transfected (FIG. 13) or Nox1 hybrid system-transfected Cos cells (FIG. 14) treated with phorbol ester (PMA) was evaluated. A differential effect of the compounds was observed with regard to each cell system. While compound 11g inhibited PMA-stimulated ROS-production in Nox2 and the Nox1 hybrid system equally well, compound 11h did not. In contrast, compound 11h did not significantly inhibit the Nox1 hybrid system, implying that compound 11h binds to p47$^{phox}$ in a way that does not interfere with the formation of an active Nox2-p22$^{phox}$-p47$^{phox}$ complex (FIG. 14).

Pre-Clinical Potential.

Figure 15:
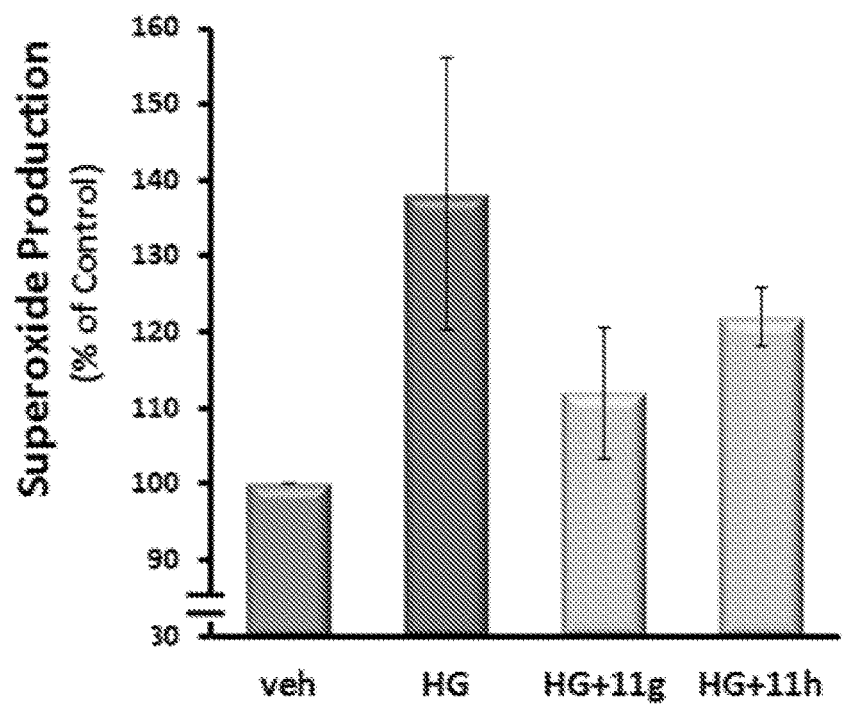
FIG. 15 is a graph showing the effects of 25 µM compound 11g and compound 11h on ROS production of rat neonatal cardiomyocytes treated with high glucose (25 mM).
Figure 16:
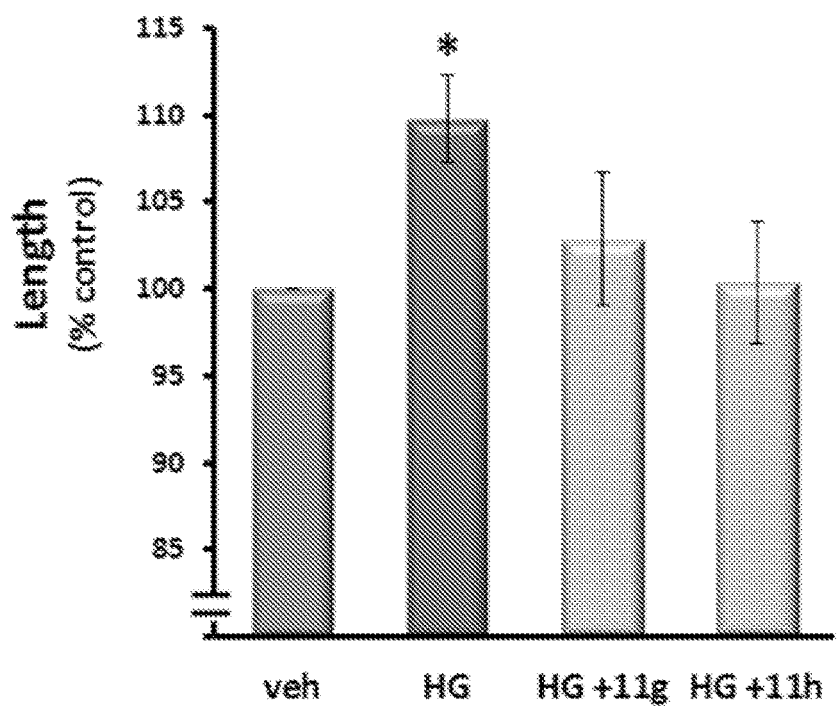
FIG. 16 is a graph showing the effects of 25 µM compound 11g and compound 11h on hypertrophy of rat neonatal cardiomyocytes treated with high glucose (25 mM).

To evaluate the pre-clinical potential of compounds 11g and 11h, the effects of high levels of glucose, which induce the generation of reactive oxygen species in cardiomyocytes and may contribute to the development of cardiomyopathy in diabetes, were evaluated. The data suggested that compounds 11g and 11h ameliorated high glucose (25 mM)-dependent ROS production in rat cardiomyocytes (FIG. 15). Furthermore, both compound 11g and compound 11h were able to reduce cardiomyocyte hypertrophy associated with high glucose challenge (FIG. 16).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A compound having a structure according to general formula I or a pharmaceutically acceptable salt thereof:

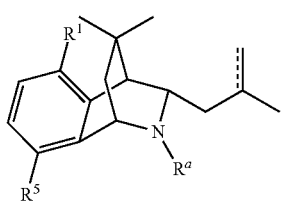

(I)

wherein "======" represents a single or double bond;
R$^1$ is hydrogen, halogen, lower aliphatic, substituted or unsubstituted aryl, or substituted or unsubstituted heteroaryl;
R$^a$ is hydrogen, —CH$_2$R$^2$, R$^3$, or —SO$_2$R$^4$;
R$^2$ is C$_4$alkyl, substituted or unsubstituted aryl, or substituted or unsubstituted heteroaryl;
R$^3$ is substituted or unsubstituted aryl, or substituted or unsubstituted heteroaryl;
R$^4$ is lower aliphatic, or substituted or unsubstituted aryl; and
R$^5$ is hydrogen, halogen, or lower aliphatic, provided that: when R$^1$ is bromo or hydrogen, then R$^a$ is not hydrogen.
2. The compound of claim 1, wherein:
R$^1$ is hydrogen, halogen, or substituted or unsubstituted aryl;
R$^2$ is C$_4$alkyl, substituted or unsubstituted aryl, or substituted or unsubstituted heteroaryl;
R$^4$ is lower alkyl, or substituted or unsubstituted aryl; and
R$^5$ is hydrogen or halogen.
3. The compound of claim 2, wherein R$^1$ is halogen.
4. The compound of claim 2, wherein R$^1$ is bromo.
5. The compound of claim 1, wherein R$^a$ is —CH$_2$R$^2$ and R$^2$ is C$_4$alkyl, substituted or unsubstituted C$_6$ aryl, or substituted or unsubstituted C$_3$-C$_5$ heteroaryl.

6. The compound of claim 1, wherein the compound is

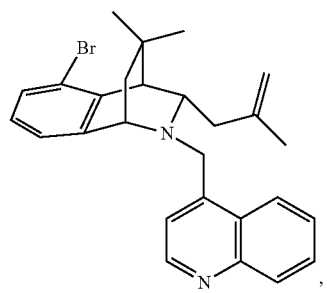

,

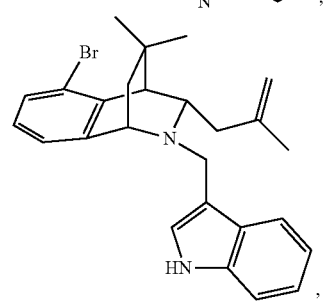

,

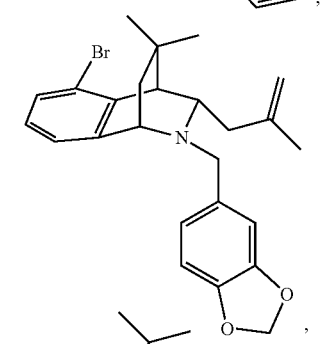

,

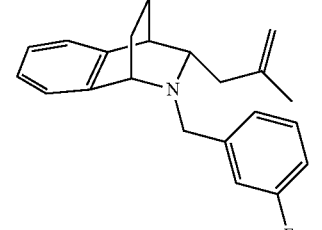

,

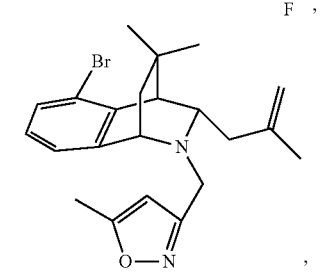

,

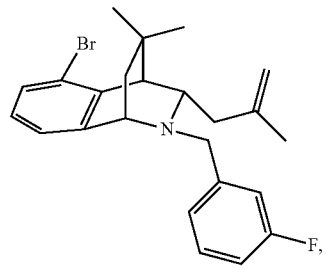

,

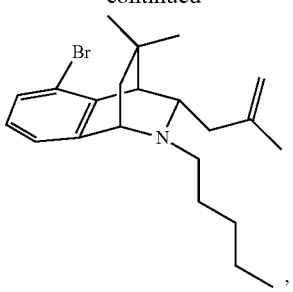

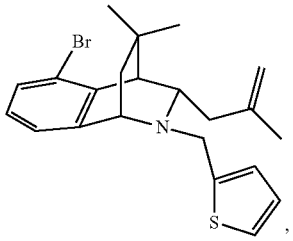

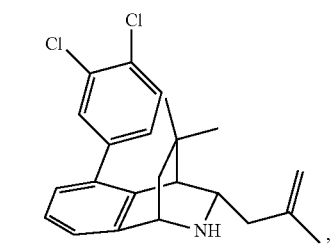

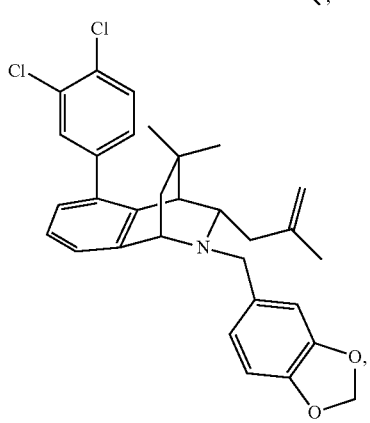

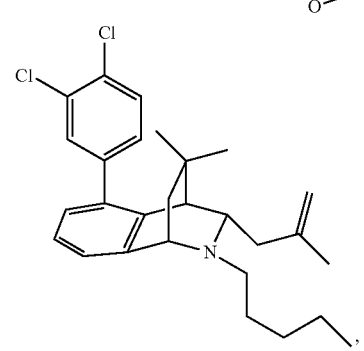

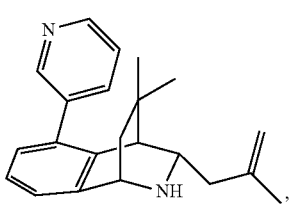

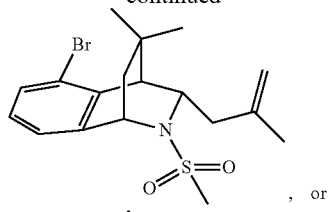

, or

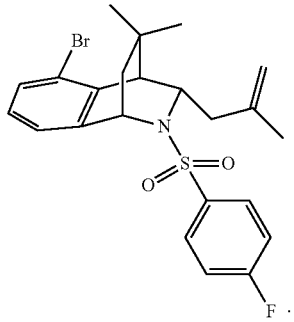

7. The compound of claim 1, wherein the compound is

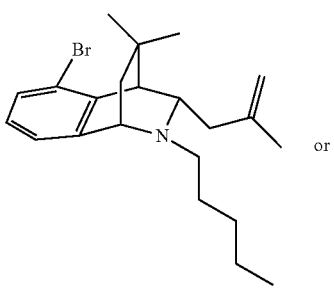

or

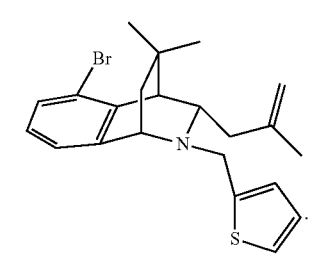

8. A pharmaceutical composition, comprising:
   at least one compound according to claim 1, or a pharmaceutically acceptable salt thereof; and
   one or more pharmaceutically acceptable additives.

9. A method for selectively inhibiting nicotinamide adenine dinucleotide phosphate oxidase 2 (Nox2), the method comprising contacting a cell with an effective amount of a compound according to claim 1 or a pharmaceutically acceptable salt thereof.

10. The method of claim 9, wherein the cell is contacted with the compound in vitro.

11. The method of claim 9, wherein contacting the cell with an effective amount of the compound reduces a level of reactive oxygen species production in the cell compared to a cell not contacted with the compound.

12. The method of claim 9, wherein the compound is
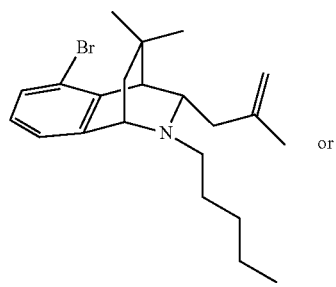 or
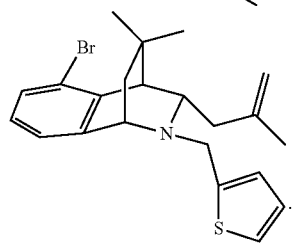.
* * * * *